United States Patent
Grody et al.

(10) Patent No.: US 8,603,745 B2
(45) Date of Patent: Dec. 10, 2013

(54) ARTIFICIAL MUTATION CONTROLS FOR DIAGNOSTIC TESTING

(75) Inventors: Wayne W. Grody, Pacific Palisades, CA (US); Michael R. Jarvis, Los Angeles, CA (US); Ramaswamy K. Iyer, Gahanna, OH (US); Laurina O. Williams, Lawrenceville, GA (US)

(73) Assignees: The United States of America as represented by the Secretary of the Department of Health and Human Services, Center for Disease Control and Prevention, Atlanta, GA (US); The Regents of the University of California, Oakland, CA (US)

( * ) Notice: Subject to any disclaimer, the term of this patent is extended or adjusted under 35 U.S.C. 154(b) by 1880 days.

(21) Appl. No.: 10/598,589

(22) PCT Filed: Mar. 11, 2005

(86) PCT No.: PCT/US2005/008108
§ 371 (c)(1),
(2), (4) Date: Sep. 5, 2006

(87) PCT Pub. No.: WO2005/086938
PCT Pub. Date: Sep. 22, 2005

(65) Prior Publication Data
US 2007/0072189 A1  Mar. 29, 2007

Related U.S. Application Data

(60) Provisional application No. 60/552,979, filed on Mar. 11, 2004.

(51) Int. Cl.
*C12Q 1/68* (2006.01)
*C12P 19/34* (2006.01)
*C12N 15/64* (2006.01)
*C12N 15/00* (2006.01)
*C07H 21/04* (2006.01)

(52) U.S. Cl.
USPC ........ 435/6.11; 435/91.4; 435/91.5; 435/440; 536/23.5

(58) Field of Classification Search
None
See application file for complete search history.

(56) References Cited

U.S. PATENT DOCUMENTS 6,531,588 B1 * 3/2003 Johnston-Dow et al. .... 536/24.3
6,607,911 B2 8/2003 Gordon et al.

FOREIGN PATENT DOCUMENTS

WO   WO 00/46401 A1   8/2000
WO   WO 2005/056768 A2   6/2005

OTHER PUBLICATIONS

Keller, G.H. et al. Journal of Clinical Microbiology 28(6):1411-1416 (Jun. 1990).*
GibcoBRL, "Salmon Sperm DNA solution," Rev. 040901, 4 pages (Apr. 2001).*
Richards, C.S. et al. Genetics in Medicine 4(5):379-391 (Sep./Oct. 2002).*
Schurmann, M. et al. European Journal of Human Genetics 10:729-732 (2002).*

(Continued)

*Primary Examiner* — Diana Johannsen
(74) *Attorney, Agent, or Firm* — Klarquist Sparkman, LLP

(57) ABSTRACT

Disclosed are artificial compositions that can be used as positive controls in a genetic testing assay, such as a diagnostic assay for a particular genetic disease. Such controls can be used to confirm the presence or absence of a particular mutation. Also provided are methods of generating such compositions, and methods of their use.

10 Claims, 4 Drawing Sheets

(56) References Cited

OTHER PUBLICATIONS

Hughes et al., "Expression profiling using microarrays fabricated by an ink-jet oligonucleotide synthesizer," *Nat. Biotechnol.* 19:342-347, 2001.

Poster presented at "American College of Medical Genetics" meeting, Mar. 2003, (10 pages).

Grant et al., "SNP Genotyping on a Genome-Wide Amplified DOP-PCR Template," *Nucl. Acids Res.* 30, e125 (2002).

Grody, "Quest for Controls in Molecular Genetics," *J. Mol. Diagnos.* 5:209-211 (2003).

Jarvis et al., "A Novel Method for Creating Artificial Mutant Samples for Performance Evaluation and Quality Control in Clinical Molecular Genetics," *J. Mol. Diagn.* 7:247-251 (2005).

Richards and Grody, "Alternative Approaches to Proficiency Testing in Molecular Genetics," *Clin. Chem.* 49:717-718 (2003).

Han-Wook et al., "Comparison of Enzyme and DNA Analysis in a Tay-Sachs Disease Carrier Screening Program," *J. Korean Med. Science*, vol. 8, pp. 84-91, 1993.

Rommens et al., "cAMP-inducible chloride conductance in mouse fibroblast lines stably expressing the human cystic fibrosis transmembrane conductance regulator," *Proc. Natl. Acad. Sci.*, vol. 88, pp. 7500-7504, Sep. 1991.

\* cited by examiner

SEQUENCE LISTING

<160> NUMBER OF SEQ ID NOS: 6

<210> SEQ ID NO 1
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 1
tggggaggga aatagatggg aaaaggtaat                                    30

<210> SEQ ID NO 2
<211> LENGTH: 27
<212> TYPE: DNA

```
<213> ORGANISM: Artificial Sequence
<220> FEATURE:
<223> OTHER INFORMATION: Oligonucleotide primer

<400> SEQUENCE: 2
ttacaagcca agcagagcat agaaagg                                           27

<210> SEQ ID NO 3
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 3
aaatgccagg tacccacatg cactatgcca                                        30

<210> SEQ ID NO 4
<211> LENGTH: 30
<212> TYPE: DNA
<213> ORGANISM: Artificial Sequence
<220> FEATURE:
<223> OTHER INFORMATION: Oligonucleotide primer

<400> SEQUENCE: 4
tcttcatttt cttctctgct cctctctacc                                        30

<210> SEQ ID NO 5
<211> LENGTH: 24
<212> TYPE: DNA
<213> ORGANISM: homo sapiens

<400> SEQUENCE: 5
aaaaacacca caaagaaccc tgag                                              24

<210> SEQ ID NO 6
<211> LENGTH: 23
<212> TYPE: DNA
<213> ORGANISM: Homo sapiens

<400> SEQUENCE: 6
aaaaacacca caagaaccct gag                                               23
```

ARTIFICIAL MUTATION CONTROLS FOR DIAGNOSTIC TESTING

CROSS REFERENCE TO RELATED APPLICATION

This is the U.S. National Stage of International Application No. PCT/US2005/008108, filed Mar. 11, 2005 (published in English under PCT Article 21(2)), which claims the benefit of U.S. Provisional Application No. 60/552,979 filed Mar. 11, 2004, herein incorporated by reference in its entirety.

ACKNOWLEDGMENT OF GOVERNMENT SUPPORT

This invention was made with U.S. Government support of Grant no. 200-2000-10030 from the Centers for Disease Control and Prevention. The U.S. Government has certain rights in this invention.

FIELD

This application relates to positive control samples that can be used in diagnostic genetic testing, methods of generating such samples, and methods of their use.

BACKGROUND

The rapid pace of disease gene discovery, fueled by the Human Genome Project, has in turn fueled a continuous expansion in the number of analytes tested by molecular diagnostic laboratories, especially those involved in heritable disease testing. Some have questioned whether the time interval from gene discovery to clinical test translation may be shorter than desired for full understanding of the test's clinical utility.

Yet even if that need were satisfied, the speed of new test development and the sheer number of genes and mutations targeted for analysis have led to another bottleneck: the lack of well-characterized control materials containing mutations of interest (Williams et al. *Arch. Pathol. Lab. Med.* 127:1353-8, 2003). These materials are used as positive controls in the assays, for test research and development, for test validation and evaluation, and as resources for quality assurance programs such as the nationwide and international proficiency testing programs offered jointly by the College of American Pathologists (CAP) and the American College of Medical Genetics (ACMG) (Grody, *Diagn. Molec. Pathol.* 3:221-3, 1994; Dequeker et al. *Nature Rev. Genet.* 2:717-23, 2001; Richards and Grody, *Clin. Chem.* 49:717-8, 2003) and performance evaluation programs offered by CDC (see the Model Performance Evaluation Program (MPEP) on the CDC website).

Procurement of these control materials from natural sources is hampered by the rarity of many target mutations, the limited quantity in clinical specimens, the dependence on clinicians to recognize the need and take the initiative to deposit patient samples in existing repositories (such as the Coriell Institute), and regulatory governing such as informed consent, sample ownership, and genetic privacy. The lack of easily accessible, validated mutant controls has proven to be a major obstacle to the advancement of clinical molecular genetic testing. Therefore, there is a need for alternative controls that can serve this purpose.

SUMMARY

The lack of readily available, patient-derived materials for molecular genetic testing of genetic disorders creates a major impediment for laboratory proficiency and quality control procedures. The compositions and methods provided herein provide an alternative to patient-derived mutation-positive samples. The disclosed compositions and methods provide synthetic samples containing mutations of interest that have been designed to resemble natural human samples. The disclosed compositions function as acceptable and realistic performance evaluation controls and quality control reagents for diagnostic and clinical laboratories, and therefore can serve as a reliable substitute for conventional patient-derived mutant samples. The compositions and methods also can provide a consistent and renewable source of positive control materials, thereby providing the potential for a permanent resource. For example, the disclosed compositions can be propagated, maintaining the fidelity of the target sequences indefinitely.

In particular examples, the disclosed compositions and methods are relatively simple, robust, and reproducible, and are applicable to the production of a wide variety of mutation samples for many genes and diseases. Specific examples include, but are not limited to: genetic and non-genetic diseases (for example cancer markers), pathogen and host markers of infectious disease, microbial antibiotic resistance genes, and molecular-based microbial typing and subtyping. Controls can be used individually or in sets, for example in a molecular genetic test or an infectious disease test.

The disclosed compositions and methods can reduce or eliminate the need to identify and approach actual patients for genetic material, and can be used to prepare a synthetic target sequence with any mutation desired (such as those that cause a genetic disorder), no matter how rare. Although particular examples are disclosed herein using the cystic fibrosis gene (CFTR), the disclosure is not limited to sequences that contain CFTR and mutations that cause cystic fibrosis. Indeed, the disclosed compositions and methods can be used to generate synthetic nucleic acid molecules containing any mutation in any gene of interest, such as a mutation that causes disease.

Disclosed herein are compositions that can be used as a positive control, for example in a diagnostic assay to screen for one or more genetic mutations, such as those that cause or result in disease. In particular examples, such compositions include no subject-derived material; that is, they contain only artificially or synthetically generated nucleic acid molecules. In one example, the composition includes a synthetic target sequence that includes at least one mutation (such as one mutant allele) and a synthetic target control sequence (such as a wild-type sequence) that encompasses a gene region of interest. For example if the target mutation is a heterozygous mutation, the synthetic target sequence can include the nucleic acid molecule that includes a mutated allele, while the synthetic target control sequence includes the corresponding wild-type nucleic acid molecule (at least at the position where the mutation would occur on the other nucleic acid strand). In a particular example, the synthetic target sequence that includes at least one mutation and the synthetic target control sequence that includes a gene region of interest are on separate nucleic acid molecules and in some examples the separate molecules are present in the composition at a 1:1 molar ratio (to represent a heterozygous mutation). In some examples, the composition further includes carrier DNA, for example to increase the DNA concentration in the composition to a desired background concentration that mimics the concentration of background DNA in a control sequence obtained from a naturally occurring biological source.

In another example, the composition includes carrier DNA and a synthetic target sequence that includes at least one mutation, for example a mutation in two alleles. For example if the target mutation is a homozygous mutation, the synthetic target sequence can include a nucleic acid molecule that includes mutations at both alleles. Carrier DNA is included in the composition to increase the total DNA concentration to the target amount. In some examples, the composition further includes a synthetic target control sequence (such as a wild-type sequence) that encompasses a gene region of interest. In a particular example, the synthetic target sequence that includes at least one mutation and the synthetic target control sequence that includes a gene region of interest are on separate nucleic acid molecules and in some examples the separate molecules are present in the composition at a 2:1 molar ratio (for example to represent a homozygous mutation).

In particular examples, the mutation in the synthetic target sequence is associated with a genetic disorder, such as a genetic disease (such as cystic fibrosis), including a non-hereditary disease (such as an acquired non-hereditary cancer marker). In another example, the mutation in synthetic target sequence is associated with a mutated microbe. In yet another example, the mutation in synthetic target sequence is associated with anti-drug resistance, such as increased or decreased resistance to an antimicrobial agent (such as an antibiotic or anti-viral agent), or to an anti-cancer agent (such as a chemotherapeutic agent).

The synthetic target sequence that includes at least one mutation can be a linear nucleic acid molecule, such as an oligonucleotide, or part of a vector, such as a plasmid or artificial chromosome. The length of the synthetic target sequence that includes at least one mutation is ideally long enough to permit detection of the mutation by the diagnostic method to be used. In a particular example, the synthetic target sequence that includes at least one mutation is at least 200 nucleotides in length, such as at least 2000 nucleotides, such as 200-4000 nucleotides. The synthetic target sequence that includes at least one mutation can include the mutation in the heterozygous, hemizygous, or homozygous state.

The synthetic target control sequence that includes a gene region of interest can include the full-length gene, or a fragment thereof. For example, the gene region of interest can include one or more fragments of the gene where mutations associated with disease occur. If multiple mutations in a gene are known to be associated with a particular disease, fragments of the gene that include each region associated with a mutation can be joined together (for example via ligation or chemical synthesis of the target sequence). In particular examples, the synthetic target control sequence that includes a gene region of interest is part of an artificial chromosome.

Also provided are methods for making a composition. In particular examples, the method can be used to generate positive control samples for quality control, including performance evaluation, proficiency testing and assay quality control, as well as genetic test evaluation and validation. In particular examples, the method includes combining a synthetic mutated target sequence with a separate synthetic target control sequence that encompasses a gene region of interest to form an artificial positive control. Such a control can also include separate carrier DNA to increase the DNA to a desired amount. In another example, the method includes combining a synthetic mutated target sequence with carrier DNA to form an artificial positive control. In yet another example, the control is generated by mutating a gene in a cell, for example by homologous recombination, and the resulting cell containing the target mutation is isolated (or the nucleic acids from the cell isolated).

The carrier DNA mimics non-target DNA that is generally present in a control sample prepared from a subject, for example by providing a concentration of non-target DNA that is similar to a concentration of non-target DNA that would be present in the control sample obtained from the subject. In particular examples, the carrier DNA is obtained from a different species than the species in which the target DNA originated. The method in particular examples includes introducing a mutation into the target sequence, thereby generating a mutated target sequence, for example using recombinant technologies, mutagenesis, or by chemical synthesis. Although exemplary methods described herein (such as site-directed mutagenesis and homologous recombination) generate synthetic target sequences with the target mutation, the disclosure is not limited to such methods. In particular examples, the target control sequence that encompasses a gene region of interest includes a BAC containing the sequence of interest. Alternatively, the target control sequence that encompasses a gene region of interest can be generated by cloning the target gene region of interest and introducing it into a vector, such as an artificial chromosome.

Methods for using the disclosed compositions in a genetic diagnostic assay are also described herein. For example, the disclosed compositions can be used in a variety of mutation detection methods, such as sequencing and allele-specific oligonucleotide (ASO) hybridization. In particular examples, the method is a method of diagnosing a genetic disease in a subject. In such examples, the method can include determining whether one or more genetic mutations associated with the genetic disease is present in a sample obtained from the subject. Using the same diagnostic method, a parallel sample containing the disclosed composition (which includes a synthetic target sequence with the one or more genetic mutations of interest that were screened for in the subject sample) is analyzed to determine whether the one or more genetic mutations associated with the genetic disease is present in the disclosed composition. If the method identifies the mutation in both the subject sample and the disclosed composition, this indicates that the subject has the disease or is a carrier for the disease. If the method identifies the mutation in the disclosed composition, but not in the subject sample, this indicates that the subject does not have the disease or is not a carrier for the disease.

Also provided by the present disclosure are kits that include the disclosed compositions.

The foregoing and other objects, features, and advantages of the invention will become more apparent from the following detailed description, which proceeds with reference to the accompanying figures.

Figure 4:
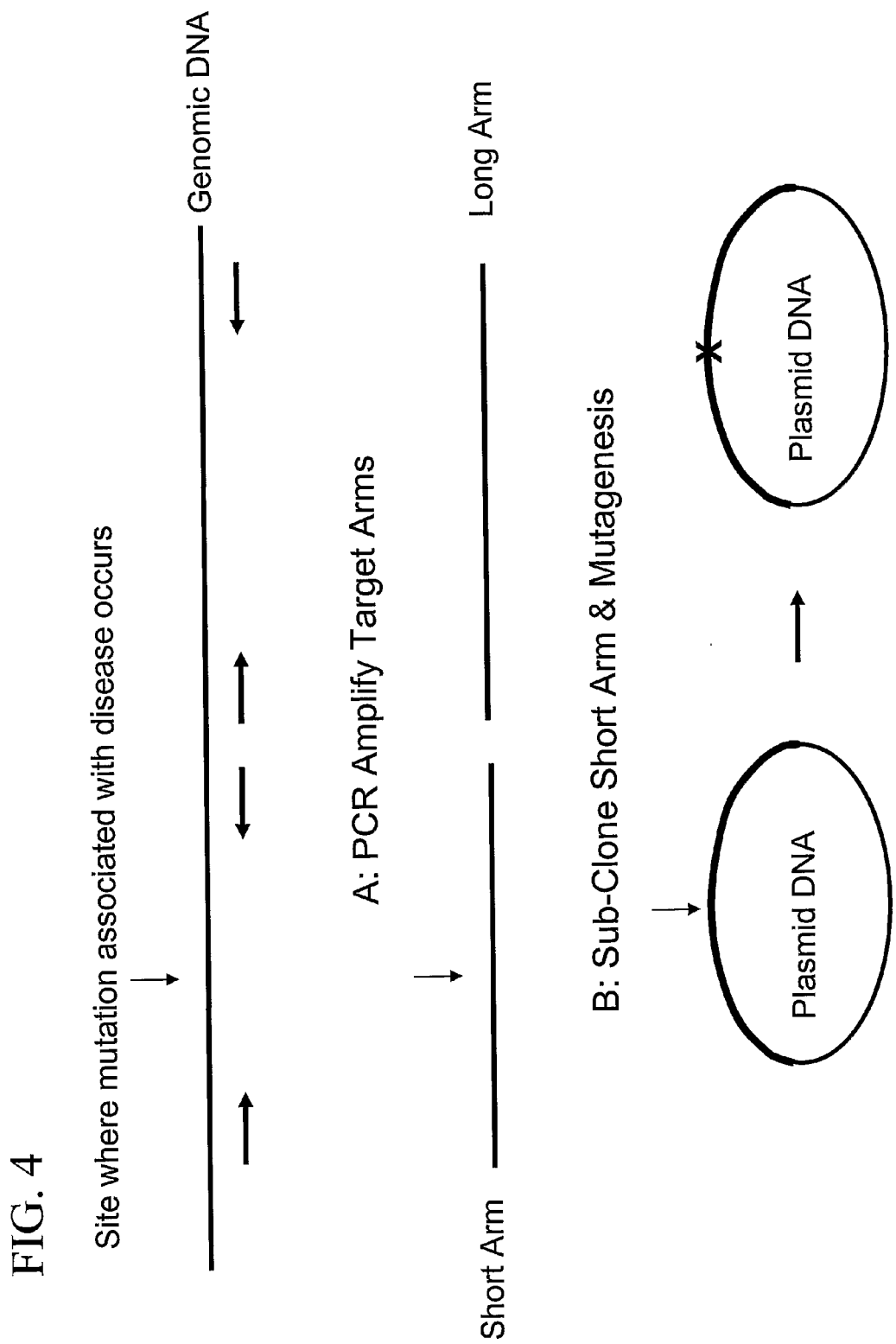

FIG. 4 is a schematic drawing showing the general strategy for amplification of CFTR target arms from genomic DNA following by plasmid cloning and site-directed mutagenesis.

SEQUENCE LISTING

The nucleic and amino acid sequences in the accompanying sequence listing are shown using standard letter abbreviations for nucleotides. Only one strand of each nucleic acid sequence is shown, but the complementary strand is understood as included by any reference to the displayed strand.

SEQ ID NOS: 1-4 show nucleic acid primer sequences.

DETAILED DESCRIPTION

Abbreviations and Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a genetic mutation" includes single or plural mutations (including deletion mutations) and is considered equivalent to the phrase "comprising at least one genetic mutation" or to the phase "comprising one or more genetic mutations." The term "or" refers to a single element of stated alternative elements or a combination of two or more elements, unless the context clearly indicates otherwise. For example, the phrase "BRCA1 or BRCA2" refers to BRCA1, BRCA2, or a combination of both BRCA1 and BRCA2. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

ASO: Allele specific oligonucleotide
BAC: bacterial artificial chromosome
MAC: mammalian artificial chromosome
PBMC: peripheral blood mononuclear cells
PCR: polymerase chain reaction
YAC: yeast artificial chromosome Allele specific oligonucleotide (ASO) analysis: A method for determining if a mutation is present in a nucleic acid sequence, such as a gene sequence. In this method, probes or primers are designed to hybridize selectively to either the normal or mutant allele. These probes are used, with two other probes, to amplify sequences across the mutation site, for example using PCR. In particular examples, the amplified DNA is applied to nitrocellulose, for example using slot-blotting. The nitrocellulose filter is then hybridized with the normal or mutant probe, generating complexes between the probe and the amplified DNA. The probe can be labeled to permit detection of the probe, for example with a radiolabel, fluorophore, or chemiluminescent compound.

The resulting complexes (or lack thereof) are analyzed to determine if a subject's amplified DNA is normal or mutated (such as deleted), or if both sequences are present. If only the normal sequence is present, then the subject does not have that specific mutation. If only the mutant sequence is detected, the subject is homozygous or hemizygous for the mutation. If both sequences are present, the subject is heterozygous for the mutation.

Amplifying a nucleic acid molecule: Increasing the number of copies of a nucleic acid molecule, such as a gene or fragment of a gene, for example a region of a gene that contains a mutation that causes disease. The resulting amplification products are called amplicons.

An example of in vitro amplification is PCR, in which a biological sample obtained from a subject (such as a sample containing PBMCs), or the disclosed positive control compositions, is contacted with a pair of oligonucleotide primers, under conditions that allow for hybridization of the primers to a nucleic acid molecule in the sample. The primers are extended under suitable conditions, dissociated from the template, and then re-annealed, extended, and dissociated to amplify the number of copies of the nucleic acid molecule. Other examples of in vitro amplification techniques include quantitative real-time PCR (such as TaqMan PCR; Applied Biosystems), strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Artificial chromosome (AC): A minimal chromosome assembled from cloned DNA sequences and coding for an origin of replication, a centromere, and telomeres. In particular examples, an artificial chromosome includes an exogenous DNA insert, such as a full-length eukaryotic gene (such as one that is about 100-300 kb), or a gene region of interest. Specific non-limiting examples of ACs include: bacterial artificial chromosomes (BACs), mammalian artificial chromosomes (MACs), P-1 artificial chromosomes (PACs), and yeast artificial chromosomes (YACs).

Artificial or synthetic nucleic acid molecule: A DNA or RNA molecule obtained or generated ex vivo or in vitro, for example by recombinant methods (such as cloning and site-directed mutagenesis) or by chemical synthesis.

Bacterial artificial chromosome (BAC): A nucleic acid construct that is based on a bacterial sex or fertility plasmid, such as the *E. coli* fertility factor (F-factor), into which exogenous DNA inserts can be inserted for transforming and cloning in bacteria. Inserts that are very large (such as those at least 100 kilobases, kb, such as 100-300 kb) can be inserted. BACs thereby allow entire eukaryotic genes (including flanking regulatory regions) to be encompassed in a single clone. For a review, see Mejia et al. (*Genome Res.* 7:179-86, 1997).

Carrier DNA: DNA, such as genomic DNA, that is included in a sample or composition (such as a sample or composition in a diagnostic assay) to increase the concentration of total amount of DNA present to a target concentration. For example, the total amount of DNA present in a sample can be a concentration of DNA that is similar to a concentration that would be present in a sample obtained from the subject. In particular examples, the amount of carrier DNA included in a composition is at least 1 µg/20 µl, such as at least 20 µg/20 µl, such as at least 50 µg/20 µl. In one example the concentration is 50 µg/20 µl. in particular examples, the carrier DNA is present in a range of 1-50 µg/20 µl, for example 20-50 µg/20 µl.

In one example, carrier DNA is of a different species that that in the subject sample, to reduce cross-reactivity with primers used in the diagnostic assay. For example, if the subject is a human, in particular examples non-human carrier DNA is used, such as salmon sperm DNA, calf thymus DNA, mouse DNA, rabbit DNA, herring sperm DNA, *E. coli* DNA, *Saccharomyces* DNA, or bacteriophage M13 DNA. In another example, if the subject is a cow, in particular examples non-cow carrier DNA is used, such as human placenta DNA. In some examples, carrier DNA is sheared.

Deletion of a nucleotide or amino acid: The removal of one or more nucleotides from a nucleic acid sequence (or one or more amino acids from a protein sequence), the regions on either side of the removed sequence being joined together.

Diagnose: To determine whether a subject has a disease or disorder, such as a disease that results from a genetic mutation. A disease can be diagnosed, for example, based on a laboratory result, such as the result of determining whether a particular mutation is present in the subject.

Dideoxy fingerprinting (ddF): A method for determining if a mutation is present in a nucleic acid sequence, such as a target or gene sequence. This method is a hybrid between dideoxy sequencing and SSCP that can detect the presence of single base and other sequence changes in PCR-amplified segments. ddF involves a Sanger sequencing reaction with one dideoxynucleotide, followed by nondenaturing gel electrophoresis. The approximate locations of the sequence changes could be determined from the ddF pattern. Genomic DNA is amplified as in SSCP with the same primer sets. Analysis can be performed manually with radioactive labeling or by fluorescent techniques on an automated sequencer.

Gene: The physical and functional unit of heredity. A gene is generally a nucleic acid sequence that encodes a peptide under the control of a regulatory sequence, such as a promoter or operator. A gene can include an open reading frame encoding a peptide, as well as exon and (optionally) intron sequences. An intron is a DNA sequence present in a given gene that is not translated into protein and is generally found between exons. The coding sequence of the gene is the portion transcribed and translated into a peptide (in vivo, in vitro or in situ) when placed under the control of an appropriate regulatory sequence. The boundaries of the coding sequence can be determined by a start codon at the 5' (amino) terminus and a stop codon at the 3' (carboxyl) terminus.

Transcriptional and translational control sequences include, but are not limited to, DNA regulatory sequences such as promoters, enhancers, and terminators that provide for the expression of the coding sequence, such as expression in a cell. A polyadenylation signal is an exemplary eukaryotic control sequence. A promoter is a regulatory region capable of binding RNA polymerase and initiating transcription of a downstream (3' direction) coding sequence. Additionally, a gene can include a signal sequence at the beginning of the coding sequence of a protein to be secreted or expressed on the surface of a cell. This sequence can encode a signal peptide, N-terminal to the mature peptide, which directs the cell to translocate the peptide.

Gene involved in (or related to) a genetic disorder: A gene (including nucleic acid molecules and the corresponding protein), mutation of which results in a disease or other disorder in a subject.

Gene region: A full-length gene or fragment thereof, such as at least 100 contiguous nucleotides of a gene. In a particular example, a gene region includes the location of the gene (and in some examples surrounding nucleotides) that when mutated, causes or is associated with a disease (such as a genetic disease).

Genetic disease: A disease or other disorder in a subject that results from a genetic mutation, such as one or more nucleic acid or amino acid substitutions, deletions, insertions, or combinations thereof. Such mutations can occur in heterozygous or homozygous states in the subject. Exemplary genetic diseases include but are not limited to: cystic fibrosis, certain cancers (such as familial breast cancer, colon cancer, and ovarian cancer), disorders that are associated with trinucleotide repeat expansions (such as Huntington disease (HD) and ataxias, for example spinocerabellar ataxia), familial Mediterranean fever (FMF), familial adenomatous polyposis (FAP), hemoglobinopathy (such as alpha-thalassemia), hereditary hemochromatosis (HH), hereditary retinoblastoma (RB), multiple endocrine neoplasia, type 2 (MEN2), venous thrombophilia, Fragile X, Connexin 26-associated deafness, canavan disease, Tay Sachs disease, achondroplasia, spinal muscular atrophy, Muenke Syndrome craniosynostosis, Kennedy disease, myotonic dystrophy, Saethre-Chotzen craniostasis, and spinal muscular atrophy. An exemplary genetic disorder is increased resistance to a therapeutic agent, such as a chemotherapeutic agent.

Insertion of a nucleotide or amino acid: The addition of one or more nucleotides to a nucleic acid sequence, or the addition of one or more amino acids to a protein sequence.

Isolated: An "isolated" biological component (such as a nucleic acid molecule, protein, or organelle) has been substantially separated or purified away from other biological components in the cell of the organism in which the component naturally occurs, such as other chromosomal and extra-chromosomal DNA and RNA, proteins and organelles. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins.

Mutation: Any change of a nucleic acid or protein sequence as a source of genetic variation, which in particular examples results in disease. For example, mutations can occur within a gene or chromosome, including specific changes in non-coding regions of a chromosome, for instance changes in or near regulatory regions of genes. Types of mutations include, but are not limited to, base substitution point mutations (such as transitions or transversions), deletions, and insertions. Missense mutations are those that introduce a different amino acid into the sequence of the encoded protein; nonsense mutations are those that introduce a new stop codon; and silent mutations are those that introduce the same amino acid often with a base change in the third position of codon. In the case of insertions or deletions, mutations can be in-frame (not changing the frame of the overall sequence) or frame shift mutations, which can result in the misreading of a large number of codons (and often leads to abnormal termination of the encoded product due to the presence of a stop codon in the alternative frame).

Nucleic acid molecule (or sequence): A deoxyribonucleotide or ribonucleotide polymer including, without limitation, cDNA, mRNA, genomic DNA, and synthetic (such as chemically synthesized) DNA. The nucleic acid molecule can be double-stranded or single-stranded. Where single-stranded, the nucleic acid molecule can be the sense strand or the antisense strand. In addition, nucleic acid molecule can be circular or linear.

The disclosure includes isolated nucleic acid molecules that include specified lengths of a gene involved in a genetic disorder, such as the full-length gene or a fragment thereof (such as an oligonucleotide). Such molecules can include at least 10, at least 50, at least 100, at least 1000, at least 2000, at least 3000, or even at least 4000 consecutive nucleotides (or more) of a gene sequence, such as from a gene region of interest (for example a region that includes the location of a mutation that can cause disease).

Nucleotide: Includes, but is not limited to, a nucleic acid monomer that includes a base linked to a sugar, such as a pyrimidine, purine or synthetic analogs thereof, or a base linked to an amino acid, as in a peptide nucleic acid (PNA). A nucleotide is one monomer in a polynucleotide. A nucleotide sequence refers to the sequence of bases in a polynucleotide.

Open reading frame (ORF): A series of nucleotide triplets (codons) coding for amino acids without any internal termination codons. These sequences are usually translatable into a peptide.

PCR (polymerase chain reaction): Describes a technique in which cycles of denaturation, annealing with primer, and then extension with DNA polymerase are used to amplify the number of copies of a target DNA sequence.

Peripheral blood mononuclear cells (PBMCs): Cells present in the blood that have one round nucleus. Examples include lymphocytes, monocytes, and natural killer cells.

Plasmid: A type of vector which is capable of autonomously replicating. Plasmids are extrachromosomal DNA molecules, which can be circular and double-stranded DNA. Plasmids can include an exogenous or foreign DNA sequence, such as a target DNA sequence that includes a mutation (such as a mutation associated with disease), or other gene region of interest.

Purified: The term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation. Similarly, a purified oligonucleotide preparation is one in which the oligonucleotide is more pure than in an environment including a complex mixture of oligonucleotides.

Recombinant: A recombinant nucleic acid molecule is one that has a sequence that is not naturally occurring or has a sequence that is made by an artificial combination of two otherwise separated segments of sequence. In particular examples, this artificial combination is accomplished by chemical synthesis or by the artificial manipulation of isolated segments of nucleic acid molecules, such as by genetic engineering techniques.

Sample: A biological specimen, such as one that contains nucleic acid molecules (such as cDNA or mRNA), proteins, cells, or combinations thereof. Exemplary samples include, but are not limited to: peripheral blood, plasma, serum, urine, saliva, tissue biopsy, pulmonary washings, expectorated sputum, buccal samples (such as brushes, swabs, and mouthwashings), surgical specimen, amniocentesis samples, chorionic villi samples, cells (such as cell lines and cell pellets), and autopsy material. In one example, a sample includes peripheral blood mononuclear cells (PBMCs). In particular examples, a sample includes a combination or mixture of sample types, or "mock" samples such as dilutions and mixtures of sample materials, and artificially-derived samples.

Single-Stranded conformation polymorphism (SSCP) analysis: A method which can be used to determine if a mutation is present, for example in a target sequence. In this method, mutations are detected by analyzing the conformational change in a DNA due to the mutation. Briefly, genomic DNA is isolated from a subject and the region containing the mutation is amplified, for example using PCR. The primers used in the PCR reaction can be labeled to label the DNA fragments, or the DNA can be directly visualized by silver staining. The resulting fragments are separated, for example by electrophoresis on a polyacrylamide gel. The bands from the normal sample will have a different electrophoretic mobility than the mutant or carrier samples. The samples can be analyzed by sequencing.

Subject: Living multi-cellular vertebrate organisms, including human and veterinary subjects. Particular examples of veterinary subjects include domesticated animals (such as cats and dogs), livestock (for example, cattle, horses, pigs, sheep, and goats), laboratory animals (for example, mice, rabbits, rats, gerbils, guinea pigs, and non-human primates), as well as birds, reptiles, and fish.

Target sequence: A sequence of nucleotides located in a particular region in a genome that corresponds to one or more specific genetic mutations, such as one or more nucleotide substitutions, deletions, insertions, amplifications, or combinations thereof. The target can be for instance a coding sequence, the non-coding strand that corresponds to a coding sequence, or a sequence 5' or 3' of the coding sequence. Examples of target sequences include those sequences associated with genetic disease.

Transgene: An exogenous nucleic acid sequence, which can be supplied to a cell by a vector.

Vector: An agent that can be used to transfer genetic material from one cell to another. A vector may, for example be, a nucleic acid molecule (such as DNA) originating from a virus, a plasmid, or the cell of a higher organism into which a DNA fragment can be integrated without loss of the vector's capacity for self-replication. Vectors can be used to introduce exogenous DNA into a cell, thereby permitting replication of the DNA fragment in large quantities. A vector can include nucleic acid sequences that permit it to replicate in a cell, such as an origin of replication, and can also include one or more selectable marker genes and other genetic elements. Examples of vectors include, but are not limited to: plasmids, cosmids, and artificial chromosomes.

Wild-type: A naturally occurring, non-mutated version of a nucleic acid or protein sequence. Among multiple alleles, the allele with the greatest frequency within the population is usually (but not necessarily) the wild-type. The term "native" can be used as a synonym for "wild-type." A wild-type sequence can either be obtained from a source in nature (such as a subject) or obtained synthetically by making an artificial polynucleotide having the same sequence as a naturally-occurring wild-type sequence.

Nucleic Acid Compositions

Currently, there is a lack of readily available positive controls for molecular genetic testing, especially for rare disorders and for mutations that occur infrequently. This is because positive control samples that are available use patient-derived material, which can be difficult to obtain. This makes it especially burdensome to obtain positive control samples for rare disorders or mutations that occur infrequently. The present disclosure provides compositions that can be used during genetic analysis as a positive control, which sufficiently resemble natural human samples. The disclosed compositions include synthetic nucleic acid molecules, instead of patient-derived materials that contain the target mutation. The ability to generate the target mutation artificially (for example using site directed mutagenesis, homologous recombination, or chemical synthesis) permits the generation of a variety of positive control samples, such as samples that include a rare mutation, such as a mutation in a rare disease (for example retinoblastoma), or a mutation in a common genetic disease that occurs infrequently (for example the 1078delT mutation of CFTR that is associated with cystic fibrosis). The disclosed compositions and methods can reduce the necessity to generate control samples from subjects having a target mutation. In addition, the compositions and methods provide a consistent and renewable source of positive control materials. In particular examples, disclosed compositions can be propagated, thereby maintaining the fidelity of the target sequences indefinitely.

In particular examples, the disclosed compositions include a synthetic target sequence and a synthetic target control sequence, which can either be present on a single polynucleotide molecule (such as present in a single oligonucleotide or a single vector), or on separate polynucleotide molecules (such as two different oligonucleotides or on two separate vectors). The target sequence includes one or more mutations (such as in one or two alleles), and the synthetic target control sequence encompasses a gene region of interest (for example to serve as a positive control for a heterozygous mutation). Such a composition in some examples also includes carrier DNA, which provides a total DNA concentration in the sample at a target level. In other examples, the disclosed compositions include a synthetic target sequence with one or more mutations (such as mutations in two alleles) and carrier DNA (for example to serve as a positive control for a homozygous mutation). In some examples, such compositions further include a synthetic target control sequence encompassing the gene region of interest.

The mutated synthetic target sequence can be a linear nucleic acid molecule, such as an oligonucleotide that includes the one or more mutations. In other examples, the mutated synthetic target sequence is a circular nucleic acid molecule, for example as part of a vector, such as a plasmid or artificial chromosome. Similarly, the synthetic target control sequence that encompasses a gene region of interest can be part of a vector, such as an artificial chromosome. The synthetic target control sequence that encompasses a gene region of interest includes a wild-type sequence at the position of the one or more target mutations. For example, if the target mutation is the ΔF508 CFTR mutation, the control sequence would include the wild-type sequence at this position. However, the control sequence could include other mutations in the sequence that is not being diagnosed in the particular assay. For example, if the target mutation is the ΔF508 CFTR mutation, the control sequence could include a mutation not associated with cystic fibrosis, or another CFTR mutation associated with cystic fibrosis (such as del1078T) that is not being screened for in the particular assay.

Synthetic Target Sequences with a Mutation

The synthetic target sequence can be any length that permits detection of the mutation by the diagnostic assay of interest. For example, if the diagnostic assay requires amplification of a nucleic acid sequence, the synthetic target sequence is long enough to permit hybridization to primers and subsequent amplification by the diagnostic method of interest. Similarly, if the synthetic target sequence is to be digested with restriction enzymes, the target sequence is long enough to include the appropriate restriction sites. In particular examples, the synthetic target sequence with one or more mutations includes at least 100 nucleotides, such as at least 200 nucleotides, at least 500 nucleotides, at least 1000 nucleotides, at least 1500 nucleotides, at least 2000 nucleotides, or at least 3000 nucleotides, such as 100-4000 nucleotides, 100-1000 nucleotides, 100-200 nucleotides, 2000-3000 nucleotides, or 2000-4000 nucleotides. In a specific example, the synthetic target sequence with one or more mutations includes at least 2000 nucleotides and is part of a plasmid.

The synthetic target sequence includes at least one mutation, such as at least one, at least two, at least three, at least four, at least five, at least ten, at least 15, or at least 20 mutations. Such mutations can be present on a single nucleic acid molecule, for example a single synthetic oligonucleotide containing at least two mutations in the target sequence. In another example, individual mutations are present in different nucleic acid molecules, such as individual oligonucleotides each with a unique mutation. In particular examples, combinations of such synthetic constructs are used. In one example, the synthetic target sequence that includes a mutation is part of a vector, and each vector includes a different mutation (or different combination of mutations) in the target sequence.

In particular examples, the mutation is generally centered within the target sequence, for example within at least 5 nucleotides of the center position of the target sequence, such as at least 10, at least 20, at least 50, or at least 100 nucleotides of the center position of the target sequence. In other examples, the mutation is near the 5' or 3' end of the synthetic target sequence, such as within at least 5 nucleotides of the 5' or 3' end of the target sequence, such as at least 10, at least 20, at least 50, or at least 100 nucleotides of the 5' or 3' end of the target sequence.

In particular examples, the mutation in the synthetic target sequence is related to a genetic disease. For example, the mutation can be known to cause or be associated with a particular disease, such as a genetic disease. Examples of genetic diseases include, but are not limited to: cystic fibrosis, cancer (such as breast cancer, colon cancer, and ovarian cancer), disorders that are associated with trinucleotide repeat expansions (such as Huntington disease (HD) and ataxias), familial Mediterranean fever (FMF), familial adenomatous polyposis (FAP), hemoglobinopathy, hereditary hemochromatosis (HH), hereditary retinoblastoma (RB), multiple endocrine neoplasia, type 2 (MEN2), and venous thrombophilia. Other non-limiting examples are provided below. Although particular examples are provided herein for detecting a mutation in a CFTR gene, the disclosure is not limited to the particular mutations disclosed, nor to the CFTR gene.

In one example, the genetic disease is a rare disease, such as hereditary nonpolyposis colon cancer (MSH2 and MLH1 genes, plus others), multiple endocrine neoplasia type 2 (RET protooncogene), familial adenomatous polyposis (APC gene), retinoblastoma (RB gene), Li-Fraumeni syndrome (p53 gene), and familial melanoma (p16 gene). In another example, the genetic disease is not a rare disease, but the mutation is one that rarely or infrequently occurs. Particular examples include, but are not limited to the 1078delT mutation of CFTR.

In a particular example, the genetic disease is cystic fibrosis, and the mutation is a mutation in a CFTR target sequence. A composition containing a synthetic target sequence with one or more CFTR mutations associated with cystic fibrosis can be used as a positive control in the diagnosis of cystic fibrosis, such as a molecular genetic test for particular CFTR mutations. Over 1000 mutations have been reported in the CFTR gene, most of which are extremely rare. No FDA-licensed commercial test kit complete with a comprehensive set of mutation controls is available. Large-scale population carrier screening for CF mutation carriers has recently been launched as recommended by an NIH consensus panel, the ACMG and the American College of Obstetricians and Gynecologists (Grody et al. *Genet. Med.* 3:149-54, 2001). However, in the absence of standards for the full panel of 25 recommended mutations and associated polymorphisms, the diagnostic community has been at a disadvantage in meeting routine quality assurance standards. The 25 mutations include the following CFTR mutations: ΔF508, ΔI507, 621+1G>T, G85E, 1078delT, R553X, G542X, R117H, R334W, 3849+10 kb C>T, R1162X, G551D, 1717−1G>A, R347P, 2789+5G>A, 2184delA, W1282X, A455E, 711+1G>T, 3659delC, 3120+1G>A, N1303K, R560T, 1898+1G>A, and I148T. Therefore, in one example, the disclosed composition includes one or more mutated synthetic target sequences, such that all 25 of these mutations are present. In one example, the composition includes 25 mutated synthetic target sequences, wherein each target sequence includes one of the 25 mutations. In a specific example, the mutated target sequences are part of a vector, such as a plasmid. Such compositions can be part of a kit.

Examples of mutations that can be included in the synthetic target sequence include, but are not limited to, one or more of the following CFTR mutations known to be associated with cystic fibrosis: G85E, R117H, ΔF508, 1078delT, or N1303K. Additional examples are provided herein. In specific examples, one or more of the over 1000 known CFTR mutations are present on a single nucleic acid molecule, for example a single synthetic oligonucleotide containing 1-25 mutations, 1-10 mutations, or 1-3 mutations in the target CFTR sequence. For example, a synthetic oligonucleotide that contains the G85E, R117H, and ΔF508 mutations can be used in the disclosed compositions.

In another example, individual CFTR mutations are present in different nucleic acid molecules, such as individual synthetic oligonucleotides each with a unique CFTR mutation. For example, a synthetic CFTR sequence that contains the G85E CFTR mutation, a synthetic CFTR sequence that contains the R117H CFTR mutation, and a synthetic CFTR sequence that contains the ΔF508 CFTR mutation, can be used in a positive control composition for CF. Such synthetic CFTR target sequences that include a single mutation can be part of a vector, wherein each vector includes a different mutation (or combination of mutations) in the CFTR target sequence. In a specific example, the composition includes at least 25 synthetic target CFTR sequences, each with a different CFTR mutation. Based on the mutations provided herein and which are known to those skilled in the art, other synthetic target sequences containing one or more CFTR mutations can be generated.

In another example, the genetic disease is breast cancer or ovarian cancer, and the mutation is a mutation in a BRCA1 or BRCA2 target sequence. A composition containing a synthetic target sequence with one or more BRCA1 or BRCA2 mutations associated with familial breast or ovarian cancer can be used as a positive control in the diagnosis of such cancers, and to identify carriers of such mutations (such as a molecular genetic test for particular BRCA1 or BRCA2 mutations).

Examples of mutations that can be included in the synthetic target sequence include, but are not limited to, one or more of the following BRCA1 mutations known to be associated with breast cancer or ovarian cancer: the common Ashkenazi-Jewish mutations 185delAG and 5382insC, as well as the rare (non-Jewish) mutations 1135insA, 1675delA, 1499insA, 2804delAA, and G563X. Examples of mutations that can be included in the synthetic target sequence include, but are not limited to, one or more of the following BRCA2 mutations known to be associated with breast cancer or ovarian cancer: 6174delT, 6503delTT, L2776X, A2951T, 999del5, and 4486delG. Additional examples are provided herein. In specific examples, one or more of the over 300 known BRCA1 and BRCA2 mutations are present on a single nucleic acid molecule, for example a single synthetic oligonucleotide containing 1-10 mutations, 1-5 mutations, or 1-3 mutations in the target BRCA1 or BRCA2 sequence. For example, a synthetic oligonucleotide that contains the 1135insA BRCA1 and 6174delT BRCA2 mutations can be used in the disclosed compositions.

In another example, individual BRCA1 or BRCA2 mutations are present in different nucleic acid molecules, such as individual synthetic oligonucleotides each with a unique BRCA1 or BRCA2 mutation. For example, a synthetic BRCA1 sequence that contains the 1135insA BRCA1 mutation, a synthetic BRCA1 sequence that contains the 1675delA BRCA1 mutation, and a synthetic BRCA1 sequence that contains the 1499insA BRCA1 mutation, can be used in a positive control composition to determine if such mutations are present in a subject. In another example, a synthetic BRCA2 sequence that contains the A2951T BRCA2 mutation, a synthetic BRCA2 sequence that contains the 6174delT BRCA2 mutation, and a synthetic BRCA2 sequence that contains the 4486delG BRCA2 mutation, can be used in a positive control composition to determine if such mutations are present in a subject. Such synthetic BRCA1 and BRCA2 target sequences that include a single mutation can be part of a vector, wherein each vector includes a different mutation (or combination of mutations) in the BRCA1 or BRCA2 target sequence. In a specific example, the composition includes at least 10 synthetic target BRCA1 or BRCA2 sequences, each with a different BRCA1 or BRCA2 mutation. Based on the mutations provided herein and which are known to those skilled in the art, other synthetic target sequences containing one or more BRCA1 or BRCA2 mutations can be generated.

Additional examples of genetic diseases (hereditary and non-hereditary), and exemplary mutations known to be associated with these diseases, are provided below. Also provided are examples of non-hereditary diseases and corresponding mutations, such as those that are associated with particular cancers. Based on this information as well as information related to genetic diseases and their associated mutations known to those skilled in the art, synthetic target sequences for any gene associated with a disorder and its corresponding mutations can be generated.

Sequence that Encompasses a Gene Region of Interest

The synthetic target sequence that includes the gene region of interest is included in the disclosed compositions to provide an internal negative control. This negative control sequence is used to generate a signal similar to that which would be detected in a sample obtained from a subject that does not contain the mutation detected by the assay. The synthetic target control sequence is in some examples a nucleic acid sequence typically found in a subject who does not have, or is not a carrier of, a genetic disease. For example, the control sequence can be a wild-type sequence, including polymorphic variations that exist in a population. In one example, the sequence is wild-type for the target disease, but contains a mutation associated with another disease. In yet another example, the control sequence contains a wild-type nucleic acid sequence in the region associated with the target mutation, but includes one or more other mutations associated with the target disease. For example, if the mutation to be screened is a 423G→T APC mutation (such as a method of screening for familial adenomatous polyposis), the control sequence includes the wild-type nucleotide at position 423 (G423, or a non-disease associated polymorphism), but could include one or more other APC mutations associated with FAP, such as a 1957A→G APC mutation.

In particular examples, the gene region of interest includes a length of control sequence sufficient to provide a negative (wild type) signal for the one or more mutations targeted by the particular diagnostic assay. For example, the gene region of interest can include the full-length wild-type sequence (such as when multiple mutations over a large segment of the gene are detected), or can include a fragment of the full-length wild-type sequence (such as half, a third, a quarter, a fifth, a tenth, or a 1/100 of the full-length sequence) such as when only a few (such as one, two or three) mutations are detected over a shorter segment of the gene sequence.

For example, if the diagnostic assay is used to only detect one mutation, the corresponding region of the wild-type sequence can be used, such as a sequence of at least 100 nucleotides, at least 200 nucleotides, at least 1000 nucleotides, or at least 2000 nucleotides of the wild-type sequence which include the fragment of the gene sequence that corresponds to the location where the mutation of interest is found. In another example, such as when the diagnostic assay is used to detect a few mutations, such as 2, 3, 4, or 5 mutations in a target sequence, the corresponding regions of the wild-type sequence can be used, and if needed, joined together to provide a contiguous sequence. In particular examples, each corresponding region is at least 100 nucleotides, at least 200 nucleotides, at least 1000 nucleotides, or at least 2000 nucleotides, of the wild-type sequence which include the region of the gene sequence that corresponds to the mutation of interest. In yet another example, if the diagnostic assay is used to detect numerous mutations, such as at least 10, at least 20, or even at least 30 mutations in a target sequence, the full-length wild-type gene sequence can be used.

In one example, the synthetic target control sequence is part of a vector, such as an artificial chromosome. Artificial chromosomes are typically used to "carry" exogenous DNA inserts that are very large (such as at least 100 kilobases). In particular examples, the artificial chromosome is a bacterial artificial chromosome (BAC), mammalian artificial chromosome (MAC), or yeast artificial chromosome (YAC). The synthetic target control sequence that encompasses a gene region of interest need not be present in a single vector. For example, the synthetic target control sequence can be divided between two or more vectors, such as at least two artificial chromosomes. In particular examples where a synthetic full-length control gene sequence (such as a full-length wild-type sequence) is used, it is divided between at least two artificial chromosomes.

Carrier Nucleic Acid Molecules

Carrier DNA includes any DNA that can be used to adjust the total concentration of DNA in a sample. In particular examples, carrier DNA, such as genomic carrier DNA, is used to increase the concentration of total DNA present in a sample to a target amount. The target amount will depend on the diagnostic assay used. For example, the total amount of DNA present in a sample can be a concentration of DNA that is similar to a concentration that would be obtained from a sample of the subject. In particular examples, the amount of carrier DNA included in a composition is at least 1 µg/20 µl, such as at least 20 µg/20 µl, such as at least 50 µg/20 µl. In one example the concentration is 50 µg/20 µl. In some examples, carrier DNA is fragmented, for example by subjecting it to shearing or sonication.

In order to reduce cross-reactivity with primers or other agents used in the diagnostic assay, in some examples carrier DNA is from a species different from the subject to be analyzed. For example, if the subject is a human, in particular examples non-human carrier DNA is used, such as salmon sperm DNA, calf thymus DNA, mouse DNA, rabbit DNA, herring sperm DNA, *E. coli* DNA, *Saccharomyces* DNA, or bacteriophage M13 DNA.

Vectors

As disclosed above, the synthetic target sequence that includes a mutation, and the synthetic target control sequence that encompasses a gene region of interest, can be part of a vector, such as a plasmid, cosmid, bacteriophage, animal virus, or artificial chromosome. For example, such synthetic target sequences can be ligated into a vector.

Vectors suitable for the present disclosure include any standard cloning vectors. Particular examples include, but are not limited to: pKC30 (Shimatake and Rosenberg, 1981, *Nature* 292:128), pKK177-3 (Amann and Brosius, 1985, *Gene* 40:183), pET vectors (Studiar and Moffatt, 1986, *J. Mol. Biol.* 189:113), pPNT (Stratagene, La Jolla, Calif.), and pUC18. In a specific example, viral vectors are used, such as retroviruses, adenoviruses, and Herpes virus vectors. In yet another example, a bacteriophage vector is used, such as lambda DNA (for example lambda-gt10), M13 phage vectors, and Bluscript KS+. Generally, bacteriophage vectors can accept about a 20 kb insert. In yet another example, cosmid vectors are used (which generally can accept about 30-45 kb of DNA). An exemplary cosmid vector is SuperCos1 available from Stratagene.

Artificial chromosomes can be used to "carry" exogenous DNA inserts that are very large (such as those greater than or equal to 100 kilobases, kb). Particular examples include BACs (based on *E. coli* F-factor), PACs (P-1 derived artificial chromosomes; based on bacteriophage P1 F-factor), MACs, and YACs. A review of large clones such as YACs, BACs, PACs and MACs as artificial chromosomes is provided by Monaco and Larin (*Trends Biotechnol.* 12:280-6, 1994).

Synthetic Non-Infectious Microbial Nucleic Acid Sequences

In other examples, the disclosed compositions include a synthetic non-infectious microbial nucleic acid sequence. Such compositions can be used as a positive control, for example in an assay to detect the presence of one or more mutations in a microbe (such as a bacteria, fungus, protozoa, or virus) or used as non-infectious control materials that mimic organisms in detection systems. Aliquots of cultures of the organisms themselves, or samples known to be infected with the microorganism, are typically used for controls. However, if the organism is particularly infection, in some examples such samples may require the use of cumbersome safety precautions. Although such controls could be inactivated by heat or chemicals, such treatment may result in biochemical changes which affect the result of the assay. Although PCR amplicons have also been used as controls, they do not mimic an organism in a diagnostic assay system.

Therefore, provided by this disclosure are compositions that include a synthetic non-infectious microbial nucleic acid sequence, which in some examples provides a permanent source of controls for mutations in micro-organisms. In particular examples, such sequences are at least 200 nucleotides, such as at least 500 nucleotides, at least 2000 nucleotides, or at least 4000 nucleotides. In particular examples the synthetic non-infectious microbial sequence is a non-infectious fragment of an infectious microbial gene sequence, or an infectious microbial sequence which has been mutated (rendering the sequences non-infectious). In some examples, such compositions further include non-infectious bacterial strains. In particular examples, the synthetic non-infectious microbial sequence is present in a vector, such as a plasmid. These vectors can be introduced into non-infectious, but similar strains of bacteria through bacterial transformation. Alternatively, the vectors can be used to introduce the synthetic non-infectious sequence into the genome of the host "non-infectious" bacterial strain through homologous recombination.

Methods of Generating Compositions that Include Artificial Mutations

There are several potential methods that can be used to generate artificially constructed samples (such as a sample having a mutation or a non-infectious microbial sequence), such as transient transfection, permanent transfection, site-directed mutagenesis, and genetic engineering through such techniques as homologous recombination. Although particular examples are provided for site-directed mutagenesis, recombineering and homologous recombination, one skilled in the art will recognize that other methods can be used. For example, the target mutated target sequence can be chemically synthesized, for example using a DNA synthesizer.

The disclosed methods can be used to generate artificial sequences for any mutation in any gene, such as those particularly described herein.

Site Directed Mutagenesis

Site directed mutagenesis can be use to introduce one or more target mutations into a target sequence, such as a linear DNA sequence, or a target sequence in a vector, such as a plasmid or artificial chromosome. Commercially available kits (such as those from Promega, Madison, Wis.), can be used. Briefly, two mismatched primers are used to amplify the wild-type target sequence using PCR, at least one of which introduces one or more target mutations. In particular examples where the target sequence is in a vector, the other primer destroys one of the restriction digest sequences in the multiple cloning site of the vector. As a result, only the successfully mutated plasmids will be resistant to cutting with that particular restriction enzyme.

In particular examples, the target sequence of interest is mutagenized, and if desired, ligated into a vector. In another example, the target sequence is first inserted into the vector, and subsequently mutagenized.

Homologous Recombination

Homologous recombination can be used to introduce a mutation into a target sequence, such as a target sequence present in a cell. The resulting recombinant cells are stable cell lines containing the mutant allele of interest in place of one or both of the endogenous normal alleles. Therefore, provided by the present disclosure are cells into which the target mutation has been introduced, such as one or more null mutations. These cells can be propagated and then used as cell samples to mimic blood specimens from subjects suspected of having a target mutation. In some examples, nucleic acids are purified from the cell, such as DNA (for example genomic DNA). The isolated nucleic acids can also be used to formulate a positive control composition for the target mutation.

Homologous recombination enables precise and permanent chromosomal integration of a transgene at the exact locus of the native gene. The method results in integration of only a single copy of the transgene, and the replacement (or "knockout") of the endogenous allele. The transgene, which becomes the target for mutation detection (for example by a diagnostic laboratory), will be at the exact chromosomal locus as the native gene, surrounded by the same restriction endonuclease sites. The resulting permanently transformed mutant cell line will thus contain a single mutant gene copy replacing a single wild type gene copy, resulting in realistic heterozygosity. Artificial positive control samples that include a homozygous control for a mutation can be obtained by repeating the homologous recombination with the same cell line a second time.

Homologous recombination depends on a dual selection procedure in the transfected cells. For positive selection, an antibiotic resistance gene (such as neomycin) is incorporated into the transgene construct under the control of a high-efficiency viral promoter, ensuring that integration of a single copy into the transfected cells is sufficient to confer resistance to the appropriate antibiotic (such as Geneticin, G418). For negative selection, the herpes simplex virus thymidine kinase gene (HSV-tk) can be ligated to the 3' end of the transgene construct. The presence of both markers in the construct tends to favor homologous, as opposed to random, integration events in cultures selected for resistance to both antibiotics (such as G418 and gancyclovir). For example, both types of integration could introduce the $neo^R$ gene and transform the cells to G418 resistance, but a homologous crossover should exclude the HSV-tk gene which would otherwise confer gancyclovir sensitivity.

The region encompassing the sequence of interest (such as the region which contains a mutation associated with a disease), is cloned into a cloning vector, such as the pPNT vector (Stratagene, La Jolla, Calif.). This vector can include a multiple cloning site and a $neo^R$ gene cassette (or other antibiotic resistance sequence) and linked tk gene (or other negative selection sequence). If the region encompassing the gene of interest containing the mutation is available, the mutated sequence can be cloned into the vector directly. Alternatively, for example to generate an artificial sample containing a rare mutation, site-directed mutagenesis can be used to introduce the target mutation into a wild-type sequence (for example using the Transformer system, Clontech, Palo Alto, Calif.). For example, after cloning the wild-type sequence into the plasmid, site directed mutagenesis can be used to introduce the mutation into the wild-type sequence. Briefly, two mismatched primers are used to amplify the wild-type sequence using PCR, one of which introduces the target mutation while the other destroys one of the restriction digest sequences in the multiple cloning site. Only the successfully mutated plasmids will be resistant to cutting with that particular restriction enzyme and can then go on to transform mismatch-repair-deficient BMH71-18 *E. coli* host cells, from which the mutated sequence can be grown in large amounts.

The resulting vector can be introduced into any recipient cell type. Examples of cell lines that can be used, include, but are not limited to HepG2, PZ-HPV-7, and HEK cell lines. In a specific example, the cell is a lymphoblastoid cell (such as the RGA-1 cell line). Any method can be used to introduce the homologous recombination vector into the cell, such as calcium phosphate precipitation, electroporation, or liposomal transfer (such as with Lipofectamine or the FuGENE-6 lipid reagent (Roche Molecular Biochemicals, Indianapolis)). Homologous recombinants are selected by their resistance to both antibiotics (such as G418 and gancyclovir), and the proper orientation of the transgene can be further confirmed by the PCR method described above or by Southern blot. Cell colonies screened and verified by this method can be used as a positive control in genetic diagnostic assays.

Recombineering

Recombineering (recombination-mediated genetic engineering) is a homologous recombination-based, highly efficient genetic engineering system that can be used to introduce mutations in a target sequence that is part of a vector, such as a BAC. In a particular example, a wild-type sequence is cloned into a BAC, and then mutagenized using recombineering to introduce one or more target mutations into the wild-type sequence, thereby generating a mutant target sequence. Methods of recombineering are known to those skilled in the art (for example see Zhang et al., *Nature Biotech.* 18:1314-7, 2000; Zhang et al. *Nature Genetics* 20:123-8, 1998; and Datsenko and Wanner, *Proc. Natl. Acad. Sci. USA* 97:6640-5, 2000). Reviews of recombineering can be found in Court et al. (*Annu. Rev. Genet.* 36:361-88, 2002) and Copeland et al. (*Nature Rev. Genet.*, 2:769-779, 2001).

Briefly, recombination genes found in phage lambda are used to introducing mutations into BACs (or other plasmids). Recombineering is made possible through the use of three λRed-encoded genes: exo, bet and gam. exo encodes a 5'-3' exonuclease that produces 3' overhangs from introduced double-stranded DNA targeting cassettes (dsDNA). bet encodes a pairing protein that binds to the 3' overhangs and mediates its annealing and homologous recombination with complementary DNA present on the BAC. At the same time, gam encodes an inhibitor of the *E. coli* RecBCD exonuclease and thereby protects the linear DNA-targeting cassette from degradation by RecBCD. λ Red (or the corresponding RecE and RecT genes of the prophage Rac) can be expressed from a multicopy plasmid using an inducible promoter. Alternatively, these genes can be expressed from a stably integrated defective λ prophage, where exo, bet and gam are controlled by the strong phage promoter pL, under stringent control of the temperature-sensitive repressor, cI857. In the prophage system, exo, bet and gam are not expressed when the bacteria are kept at 32° C. By shifting the bacteria to 42° C. for as little as 15 minutes, the genes are rapidly induced to very high levels and homologous recombination is very efficient.

Methods for making a mutation in a target sequence that is present in BAC are known in the art. One method is RecA dependent and relies on the use of a shuttle vector and two recombination steps: integration followed by the resolution of the co-integrate (Yang et al., *Nat. Biotechnol.*, 15:859-865, 1997 and Gong et al., *Genome Res.*, 12:1992-8, 2002). A simpler and more widely used method is based on positive/negative selection using, for example, a sacB-neo fusion gene (Zhang et al. *Nature Genetics* 20:123-8, 1998). neo (kanamycin) resistance is used for positive selection while sucrose toxicity resulting from sacB expression is used for negative selection. A related method is based on counterselection using a recognition site for a rare restriction enzyme, such as I-SceI (Jamsai et al. *Genomics* 82:68-77; 2003). A method for BAC modification without selection is also known (Swaminathan et al. *Genesis*, 29:14-21; 2001). Although relatively efficient, this method relies on a PCR-based screening of the resulting colonies to identify the target clones. A galK-based positive/negative selection system for the manipulation of BACs is described in Warming et al. (*Nucleic Acids Res.* 33(4):e36, 2005, herein incorporated by reference in its entirety with respect to introducing mutations). The *E. coli* galactose operon includes the galK gene. The galK product, galactokinase, catalyzes the first step in the galactose degradation pathway, phosphorylating galactose to galactose-1-phosphate. Galactokinase also efficiently catalyzes the phosphorylation of a galactose analog, 2-deoxy-galactose (DOG). The product of this reaction cannot be further metabolized, leading to a toxic build-up of 2-deoxy-galactose-1-phosphate. Thus, both positive and negative selection can be conferred by galK. Because galK is used for both selection steps, background following negative selection is reduced and no colony screening is required. The small size of the galK cassette (around 1200 bp plus homology arms) makes it easier to amplify by PCR and to introduce into bacteria using electroporation.

Methods of Genetic Testing

Methods are disclosed for determining whether a genetic mutation is present in a subject, for example to diagnose a disease in a subject, using the disclosed compositions as controls. The disclosed artificial compositions provide a product that mimics or is able to behave very similar to a control sample obtained from a subject in commonly used methods for molecular genetic testing. The methods can be applied to any benign heritable genetic polymorphism, any heritable disease-causing gene, as well as cancer-causing genes. Although particular examples of diseases and mutations are provided below, the disclosure is not limited to such diseases and mutations, as numerous others are known in the art.

In one example, the method includes determining whether one or more genetic mutations are present in a subject, for example by analyzing a biological sample obtained from the subject, and determining whether the one or more genetic mutations are present in the disclosed artificial positive control composition. If the mutation is detected in both the subject and the positive control sample, this indicates that the subject has the mutation. If the mutation is not detected in the subject, but detected in the positive control sample, this indicates that the subject does not have the mutation.

The one or more mutations that are screened for in the subject are also present in the disclosed artificial positive control sample. For example, if the subject is being screened for the presence of the ΔF508 CFTR mutation, the mutated target sequence in the artificial positive control sample also includes the ΔF508 CFTR mutation, and the synthetic control sequence includes a region of CFTR DNA that encodes for the F508 position. In one example, at least two mutations are screened for, wherein the artificial positive control sample includes the at least two mutations. For example, if the subject is being screened for the presence of the 1078delT and ΔF508 CFTR mutations, the mutated target sequence in the artificial positive control sample also includes the 1078delT and ΔF508 CFTR mutations, while the synthetic control sequence includes a region of CFTR DNA that encodes for the F508 position and includes the 1078T position.

In particular examples, at least two artificial positive control samples are used, each with one mutation or a particular combination of mutations. For example, if the subject is being screened for the presence of the E148Q and M694I MEFV mutation (which are associated with familial Mediterranean fever), the mutated target sequence in one artificial positive control sample can include the E148Q MEFV mutation, and the synthetic control sequence includes a region of MEFV DNA that encodes for the E148Q position, and the other artificial positive control sample can include the M694I MEFV mutation and the synthetic control sequence includes a region of MEFV DNA that encodes for the M694I position.

A variety of methods (including commonly used genetic testing platforms) can be used to determine if a particular mutation is present in a nucleic acid sequence. Although particular examples are provided, the disclosure is not limited to such methods. Particular examples of methods that can be used to detect a mutation in a subject and in an artificial positive control sample include heteroduplex analysis, amplification refractory mutation system (ARMS), oligonucltoide ligation assay (OLA), single stranded conformational polymorphism (SSCP), reverse dot blot hybridization with allele-specific probes, Southern blotting, allele-specific restriction endonuclease digestion, capillary electrophoresis, and direct sequencing.

Biological Samples

Appropriate specimens for use with the current disclosure in determining if a mutation is present in a subject, for example to diagnose a genetic disease, include any conventional clinical samples, for instance blood or blood-fractions (such as serum, white blood cells, cell pellets, or PMNLs), buccal samples (such as brushes, swabs, and mouthwashings), and prenatal samples (such as amniocytes and chorionic villi). Samples can also include cells obtained from such samples, cell lines, as well as nucleic acid preparations from such samples. Techniques for acquisition of such samples are well known in the art. Such samples can be prepared in the conventional manner.

In one example, DNA is obtained from the sample. Typically, 10 to 50 ng of subject DNA is sufficient for amplification. In one example, about 5 mL of whole blood is used for the extraction of DNA (about 30 μg) and subsequent amplification. However, if DNA is not amplified, larger amounts of blood can be collected. In one example, PBMCs are used as a source of isolated nucleic acid molecules.

Once a sample has been obtained, the sample can be used directly, concentrated (for example by centrifugation or filtration), purified, amplified, or combinations thereof. DNA can be prepared from biological samples using a variety of known extraction protocols, ranging from crude lysates to highly purified DNA. For example, rapid DNA preparation can be performed using a commercially available kit (such as the InstaGene Matrix, BioRad, Hercules, Calif.; the NucliSens isolation kit, Organon Teknika, Netherlands. In one example, the DNA preparation method yields a nucleotide preparation that is accessible to, and amenable to, nucleic acid amplification or diagnostic analysis.

Exemplary Diseases and their Mutations

Cystic fibrosis (CF). CF is the most-common lethal hereditary disease in the white population, and is caused by mutations in the cystic fibrosis transmembrane conductance regulator (CFTR) gene. Over 1200 mutations have been reported in the CFTR gene, most of which are rare. The ΔF508 mutation is the most common CFTR mutation. Additional mutations in the CFTR associated with cystic fibrosis include, but are not limited to: G85E, R117H, G149R, L206W, R334W, G551D, G542X, R553X, S945L, R1070W, N1303K, 1078delT, D1152H, 3272-26A→G, S1235R, as well as the most commonly observed allele of African origin, 3120+1G→A. In particular examples, a CFTR mutation includes one or more of the following CFTR mutations: ΔF508, ΔI507, 621+1G>T, G85E, 1078delT, R553X, G542X, R117H, R334W, 3849+10 kb C>T, R1162X, G551D, 1717−1G>A, R347P, 2789+5G>A, 2184delA, W1282X, A455E, 711+1G>T, 3659delC, 3120+1G>A, N1303K, R560T, 1898+1G>A, and I148T.

Disorders associated with trinucleotide repeat expansions: Trinucleotide repeat expansion mutations are characteristic of several neuromuscular disorders, such as fragile X syndrome, Huntington disease (HD), spinocerebellar ataxia (SCA), and Friedreich ataxia. HD is a translated polyglutamine disease, which results from CAG repeat expansions in exon 1 of a gene termed huntington (originally known as IT-15) located on chromosome 4p16.3. The range of repeat length in the unaffected population is 6-35 triplets. Repeats longer than 35 are considered expanded, and no individual with a repeat length <36 triplets has been convincingly diagnosed with HD.

Drug-resistance mutations: Mutations in a subject can provide increased or decreased resistance to a therapeutic agent, such as an anti-cancer agent. For example, mutations in the bcr-abl fusion gene are known to confer resistance to Gleevec therapy in chronic myelogenous leukemia. In addition, mutations in a pathogen (such as a bacteria or virus), can provide the pathogen with increased or decreased resistance to a therapeutic agent (such as an antibiotic or anti-viral agent). Therefore, the disclosed compositions can include a synthetic target sequence with a mutation known to be associated with resistance to a therapeutic agent. Detection of this mutation (in the subject and the positive control sample) indicates that that the subject (or microbe) has increased resistance to the therapeutic agent. If this mutation is not detected in the subject, but is detected in the positive control, indicates that that the subject (or microbe) does not have increased resistance to the therapeutic agent.

Familial Mediterranean Fever (FMF) is an inherited disease characterized by recurrent inflammatory polyserositis. Mutations in the MEFV gene that cause FMF include, but are not limited to: E148Q and M694I.

Familial adenomatous polyposis (FAP) is a rare genetic disease characterized by the development of hundreds to thousands of adenomatous polyps along the colon-rectum leading to cancer at a young age, if left untreated. Mutations in the APC (adenomatous polyposis coli) gene, have been shown to be associated with FAP. Exemplary mutations include, but are not limited to: whole APC gene deletions, deletion of exon 14, as well as exonic mutations in exon 4 (c.423G→T), exon 14 (c.1956C→T, c.1957A→G, and c.1957A→C), and exon 15 (c.1959G→A).

Familial breast and ovarian cancer: Mutations in BRCA1 (BReast-CAncer susceptibility gene 1) and BRCA2 have been found to be associated with breast and ovarian cancer. There are over 300 reported mutations and polymorphisms. There are many rare polymorphisms (Shattuck-Eidens et al. *JAMA* 278:1242-50, 1997). Particular examples of BRCA1 and BRACA2 mutations, include, but are not limited to: 1135insA, 1675delA, 1499insA, 2804delAA, and G563X for BRCA1, and 6503delTT, L2776X, A2951T, 999del5, and 4486delG for BRCA2). Additional examples include the ethnic-specific mutations, such as Ashkenazi Jewish alleles 185delAG and 5382insC in BRCA1 and 6174delT in BRCA2 (Abeliovich et al., *Am. J. Hum. Genet.* 60:505-14 1997), the African-American mutations 1832del5 and 5296del4 as well as the BRCA1 mutation 1625del5 and the BRCA2 mutations 1536del4, 6696delTC, and 7795delCT (Gao et al., *Am J. Hum. Genet.* 60:1233-6, 1997; Gao et al., *Hum. Genet.* 107:186-91, 2000), and the Scandinavian mutations 1675delA and 1135insA in BRCA1 (Borg et al., *Disease Markers* 15:79-84, 1999).

Hemoglobinopathy includes hereditary disorders of hemoglobin. Examples include α-thalassemia, β-thalassemia, and sickle cell disorders. Mutations associated with β-thalassemia in the β-globin gene include, but are not limited to GTG→GGG (Val126Gly), 39C→T, a deletion of cytosine at codons 77/78 (−C) [CAC(His) CA− or CTG(Leu)→−TG], GAG→GCG (Glu26Ala), and GGC→AGC (Gly29Ser). Mutations associated with α-thalassemia in the α2-globin gene include, but are not limited to, GGC→GGT at codon 22, and GAG→TAG (or Glu→Term) at codon 23. A mutation associated with sickle cell in the hemoglobin gene includes, but is not limited to, E→V at the sixth position of the beta chain.

Hereditary hemochromatosis (HH) is an autosomal recessive disease caused by defective iron absorption. C282Y is the most frequent HFE gene mutation causing HH in Northern European populations and their descendants. Other exemplary mutations in the HFE gene that cause HH, include, but are not limited to: H63D and S65C.

Hereditary nonpolyposis colon cancer (HPCC): Mutations in MLH1, MSH2, and MSH6 have been found to be associated with HPCC. Over 300 different alterations in MMR genes have been identified, with the majority (about 90%) in MLH1 and MSH2. Particular examples of mutations include, but are not limited to: single base pair deletions which lead to frameshift (MLH1: g.38-39insCCCA, g.1971del.T; MSH2: g.163del.C, g.746del.A; MSH6: g.3320del.A), the nonsense mutation in MSH2 g.1030C→T leads to a stop codon: p.Q344X, the MLH1 nonsense mutation g.806C→G, the 2006delAAAAG mutation in MLH1, and the deletion of two adenosine nucleotides (190-191 del AA) at codon 64 in exon 2 of the hMLH1 gene.

Hereditary retinoblastoma (RB) is an autosomal dominant disorder that results in intraocular cancer. RB is caused by mutations in the RB1 gene. Examples of mutations in RB1 that have been associated with RB, include, but are not limited to, 78250C→T, deletion of RB1, a 2 bp insertion in exon 2 (5506-5507insAG, R73fsX77), a G to A transition affecting the last invariant nucleotide of intron 13 (76429G>A), a T to C transition in exon 20 (156795T→C, L688P), C to T transitions resulting in stop codons in CGA codons (64348C→T, 76430C→T, 78238C→T, 78250C→T, and 150037C→T), K616E in exon 19 (1846A→G), an AA insertion in exon 7 (684-685insAA), R500G in exon 16 (1498A→G), and an A insertion in exon 23 (c.2391-2392insA).

Multiple endocrine neoplasia, type 2 (MEN2) is an autosomal, dominantly inherited syndrome involving endocrine tumors. Mutations of the RET proto-oncogene have been found to be associated with MEN2A. Particular examples of mutations in RET include, but are not limited to: C618S, 1900T→C(C634R), V804L, and S836S.

Non-heritable cancer markers: In addition to the hereditary cancer markers like BRCA1/2, compositions containing somatic mutations of interest that are associated with particular tumors can be generated based on the teachings in this disclosure. Examples include, but are not limited to: K-ras mutations in pancreatic cancer (such as those in codons 12 and 13), p53 mutations in lung cancer, and c-kit mutations in gastrointestinal stromal tumors (such as those in exon 11).

p53-associated disorders include those disorders that are associated with a mutation in a mutant p53 nucleic acid molecule or protein. For example, mutant p53 molecules have reduced ability to decrease or suppress tumor growth or development, the ability to regulate the cell cycle, the ability to induce apoptosis, the ability to function as a transcription factor, or combinations thereof. Exemplary mutant p53 sequences are disclosed in Yamada et al. (*Cancer Res.* 51:5800-5, 1991), Mashiyama et al. (*Oncogene* 6:1313-8, 1991) and Peller et al. (*DNA Cell Biol.* 14:983-90, 1995). In a particular example, the p53 mutation is in any of exons 4-7.

Venous thrombophilia includes disorders that result in clots forming in the venous system. Mutations in several genes are known to be associated with increased thrombosis risk, including but not limited to: substitutions in the human factor V Leiden gene (1691G→A transition that results in a Arg506Gln polymorphism; 1628 G→A transition that results in a R485K polymorphism; 1091 G→C transition that results in a Arg306Thr mutation; 1090A→G transition that results in a Arg306Gly mutation; and 4070 A→G transition that results in a His1299Arg polymorphism); fibrinogen (Thr312Ala); methylenetetrahydrofolate reductase (MTHRF)(677 C→T and 1298 A→C); and prothrombin (G20210A mutation).

Kits

The present disclosure also provides kits that include the nucleic acid molecules and compositions disclosed herein. For example, a kit can include one or more positive controls to diagnose a genetic (hereditary or non-hereditary disorder), or for example to determine if a subject or micro has increased or decreased resistance to a therapeutic agent. In particular examples, each agent of the disclosed compositions are provided in a separate container. In one example, the kit includes a separate container for each target mutation of interest.

In one example, a kit includes a set of CFTR positive control samples, such as the 25 ACMG-recommended CFTR mutations. In another example, a kit includes a set of positive controls that can be used for genetic-based thrombophilia testing (such as positive control samples for mutations in human factor V Leiden, fibrinogen, MTHRF, and prothrombin.

EXAMPLE 1

Sample Construction and Preparation

This example describes methods used to generate diagnostic samples for detecting mutations in the CFTR gene. However, the disclosure is not limited to artificial DNA samples that contain single mutations nor to only the CFTR gene. For example, using methods similar to those described in this example, multiple mutations can be make to a single target sequence through the addition of multiple characterized plasmids each containing a single mutation. In addition, a single plasmid can be manipulated to contain more than one mutation in a target sequence. The method can also be used to generate artificial sequences that include target sequences from other genes that cause disease, such as those having a mutation known to be associated with a genetic disease.

The CFTR gene is located on chromosome 7 (7q31.2). It is approximately 250 kb in size and contains 27 exons (Zielenski and Tsui, *Ann. Rev. Genet.* 29:777-807, 1995). The following mutations were used to generate artificial DNA samples: G85E (exon 3), N1303K (exon 21), and 1078delT (exon 7). G85E and N1303K represent the most 5' and 3' mutations in the original ACMG panel, respectively. 1078delT is a mutation not currently available from the Coriell repository or other accessible sources. The G85E and 1078delT target sequences are rarer and thus difficult to obtain from natural sources (such as patient samples) than N1303K; the latter was used as a marker primarily to ensure that the CFTR constructs encompassed all possible mutations in the original ACMG panel. (The 1078delT was recently removed from the core mutation screening panel because of its rarity; Watson et al. *Genet. Med.* 6:387-91, 2004).

Figure 1:
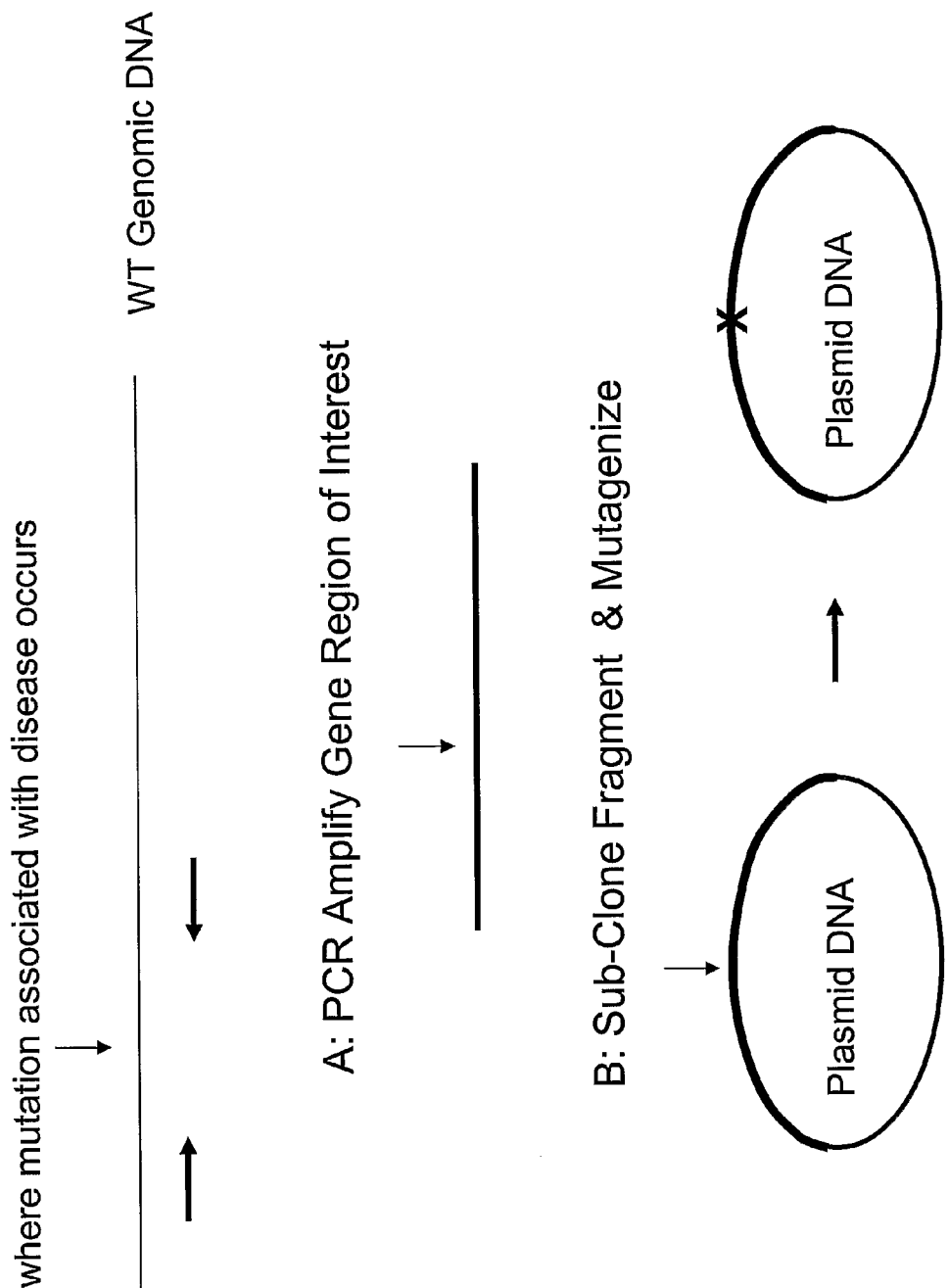
FIG. 1 is a schematic drawing showing the general strategy for amplification of a CFTR gene region of interest from genomic DNA followed by plasmid cloning and site-directed mutagenesis.

FIG. 1 illustrates the strategy used. Fragments of CFTR that would contain the mutation sites of interest (2-4 kb) were PCR amplified from human BAC DNA (ResGen, Birmingham, Ala.) containing the wild-type (non-mutated) CFTR gene. BAC clones CIT-B 068P20 (AC000111) and CIT-B 133K23 (AC000061) which together contain the complete CFTR gene and flanking sequences served as the source of CFTR nucleic acid material for PCR amplification.

Fragments of wild-type CFTR were PCR amplified, wherein the mutation site for each segment would generally center in the amplified gene product. Primer sequences 5'-tgg gga ggg aaa tag atg gga aaa ggt aat-3' (SEQ ID NO: 1) and 5'-tta caa gcc aag cag agc ata gaa agg-3' (SEQ ID NO: 2) generated a 3 kb amplicon that contained the G85 mutation site while primer sequences 5'-aaa tgc cag gta ccc aca tgc act atg cca-3' (SEQ ID NO: 3) and 5'-tct tca ttt tct tct ctg ctc ctc tct acc-3' (SEQ ID NO: 4) generated a 2.4 kb amplicon that contained the 1078 mutation site.

The resulting amplified sequences were subsequently ligated to standard cloning vectors (pCR2.1 and pCRII, Invitrogen) and subjected to one round of site-directed mutagenesis (Promega, Madison, Wis.) to introduce the target CFTR gene mutation. Plasmids containing the target CFTR sequence now containing the target mutation were identified by sequence analysis of the exon of interest and restriction digest pattern analysis.

These plasmids, containing a single CFTR mutation and flanking gene regions, served as the basis for the generation of artificial mutation samples. Large preparations of each plasmid type (with and without the mutation of interest) as well as BACs 068P20 and 133K23 were purified, characterized, and quantitated. Each artificial sample was first formulated by combining equimolar ratios of these separate DNA sources.

Since most current assays for CFTR mutations target multiple sites in the gene and not just a single target mutation, BAC DNA was included so that negative (wild type) signal would be detected for all those mutations targeted by the assay but not present in the sample. Although this adds a third allele to certain of the samples, the amount is slight enough that it does not affect the biallelic signal balance in most assays (see Example 3).

Calculations to determine the approximate concentration of each DNA source for each sample were based largely upon the relative molar concentration of each allele that would be expected in a typical CAP/ACMG proficiency sample (50 µg DNA in 20 µL buffer). [Roughly, 50 µg genomic DNA is approximately equivalent to $2\times10^{-17}$ moles of one set of human chromosomes ($3\times10^9$ base-pairs)]. To make these samples, 200 µL of 50 µg/20 µL salmon sperm DNA was mixed with 10 µL of each plasmid and 10 µL BAC DNA (for each BAC). This mixture was divided into 10 samples of 20 µL each. The plasmid concentrations were approximately 1 ng/µL, and BACs were approximately 14 pico grams/µL. The plasmids were approximately 6 kb while the BACs were 150 kb and 88 kb.

The addition of flanking DNA to the mutation site permits increased flexibility in the type of processes that can be used in detection and identification of genetic mutations. The two BAC clones make available the entire CFTR gene sequence, thereby allowing the artificial composition to more closely resemble or mimic a sample obtained from a subject.

To further make the artificial samples mimic a sample of nucleic acid molecules obtained from a subject, carrier nucleic acid molecules in the form of salmon sperm DNA was added for bulk and background genomic DNA carrier. Since it was the major DNA component, it was determined that when salmon sperm DNA was used as template for PCR analysis using any of the oligonucleotide primer sets, no amplified products of the anticipated sizes were observed by either the AMP-FLP method or a commercial CFTR hybridization assay (Roche Diagnostics, Indianapolis).

Figure 2:
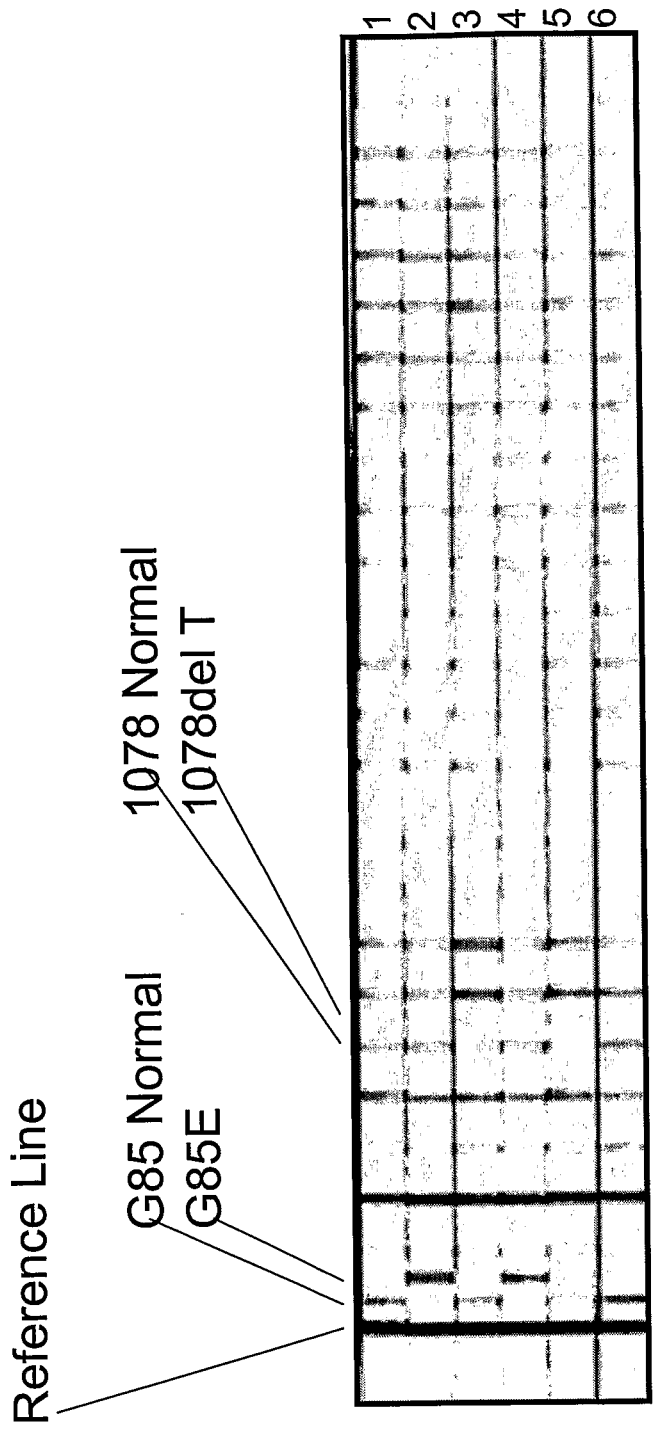
FIG. 2 is a digital image of a hybridization strip showing the results of in-house pilot testing of constructed heterozygous and homozygous products for CFTR mutations G85E and 1078delT using a commercial reverse hybridization strip system (Roche Linear Array CF Gold 1.0). Test results from an actual patient sample are also shown for comparison (strip 6). The observed genotypes are: 1, negative for tested mutations; 2, G85E homozygote; 3, 1078delT homozygote; 4, G85E heterozygote; 5, 1078delT heterozygote; 6, negative for tested mutations.

Samples were formulated and analyzed for each of the following five genotypes: wild type (homozygous normal), homozygous G85E, homozygous 1078delT, heterozygous G85E, and heterozygous 1078delT. Each sample was observed to be indistinguishable from "natural" samples (a sample obtained from a subject) when assayed with a PCR/restriction digest assay and standard reverse line blot technology (FIG. 2).

EXAMPLE 2

Confirmatory DNA Sequencing

Figure 3A:
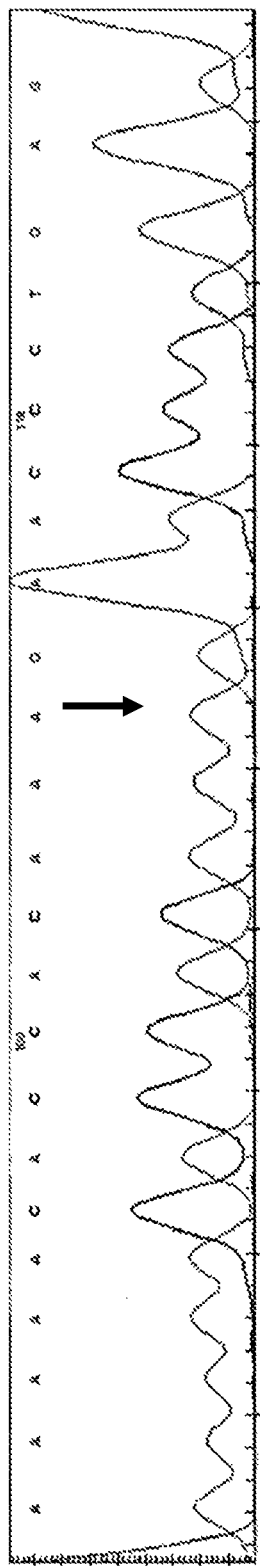
FIG. 3 is a trace showing exon 7 sequencing of wild type and 1078delT mutation-containing plasmids. Panel A shows a segment of the plasmid containing the wild type exon 7 sequence (SEQ ID NO: 5). Panel B shows the corresponding segment of the plasmid containing the 1078delT mutation (SEQ ID NO: 6). The arrows indicate the position of the T that is present in the wild type but deleted in the mutation-containing, sequence.
Figure 3B:
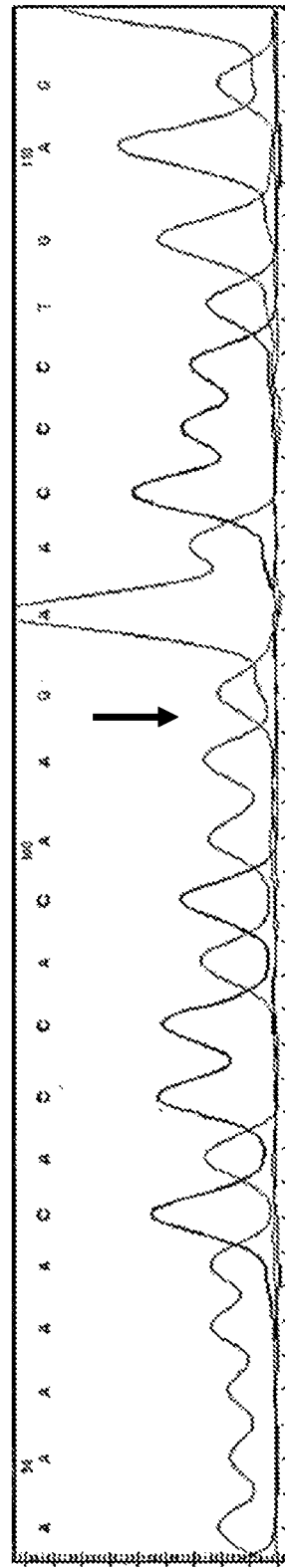

To ensure fidelity of the constructed fragments and detect the introduction of unexpected variants due to PCR misincorporation errors or other sources, plasmids containing the CFTR exon 7 with or without the 1078delT mutation were sequenced using standard ABI technology. Both the wild type and mutant sequences were present in the respective constructs with no alterations (FIG. 3).

EXAMPLE 3

Using Artificial CFTR Mutation Controls

The five artificial DNA samples generated in Example 1 were tested by nine pilot testing facilities that use a wide range of testing platforms for CFTR mutation screening. The results are summarized in Table 1.

TABLE 1

Pilot testing summary

| Sample | Lab Analysis (Correct Results/Total Results) | Unable to Analyze |
|---|---|---|
| Normal (w.t.) | 7/8 | 1 |
| G85E, heterozygous | 8/9 | |
| G85E, homozygous | 8/9 | |
| 1078delT, heterozygous | 8/9 | |
| 1078delT, homozygous | 7/9 | |

The results indicate that the five DNA testing samples were reproducible in mimicking the target human genotypes across multiple testing platforms. Although some facilities noted slight anomalies in sample behavior, only one mutation sample was incorrectly identified (as a heterozygote 1078delT instead of a homozygote). Since the five test samples were optimized using reverse dot blot technology, facilities using similar testing methods (by two different manufacturers) had little difficulty discerning the designed genotype of each sample.

Other testing platforms included the ABI Genotyper technology, a proprietary multiplex hybridization assay, amplification refractory mutation system (ARMS), and two different proprietary DNA microarray systems. Each of these platforms obtained generally correct results (Table 2), although one microarray facility reported slightly more skewing of the mutant:wild type ratios in the heterozygote samples and spurious detection of wild type sequence in the 1078delT "homozygous" sample as noted above.

TABLE 2

PILOT PERFORMANCE BY METHOD

| Method | No. of Labs | Results | Comments |
|---|---|---|---|
| Reverse ASO Line Blots | 3 | Correct | Exon 7 partial PCR failure* |
| Genotyper | 1 | Correct | Het. ratios not exactly 50:50 |
| Microarray | 2 | correct | Mostly Trace w.t. in 1078delT homo. |
| Proprietary Multiplex Assay | 1 | Correct | Some exon signals uneven |
| Sequencing | 1 | Correct | M470V polymorphism also detected |
| ARMS | 1 | Equivocal | Several extraneous mutations detected |

*one lab; did not affect interpretation

As shown in Table 2, the artificial positive control samples performed most reliably on allele-specific oligonucleotide (ASO) hybridization platforms, whether in reverse line blots or with microarray instrumentation. The reason for the observed inaccuracies is likely due to the fact that the artificial samples prepared in Example 1 were initially optimized on other platforms. For example, the artificial samples dictated that the "homozygous" samples were constituted with a trace amount of wild type sequence, and the microarray facility that detected this in the 1078delT sample stated that their platform is extremely sensitive in its allelic detection of heterozygote sequences.

The only platform which initially produced spurious results was the ARMS assay, which detected extra CFTR mutations for all five samples in addition to the ones introduced via site-directed mutagenesis. Upon further investigation it was revealed that the concentration of template DNA in the artificial samples was 10-100-fold higher than that used from patient samples in this assay. Some of the extra bands, which were rather faint to begin with, disappeared when the laboratory diluted the samples before analysis.

The one laboratory using DNA sequencing methodology was able to analyze the entire CFTR "gene" in the artificial sample, and even detected an unexpected (though common) M470V polymorphism in all samples (apparently carried by the person who donated DNA for construction of these BACs in the early years of the Human Genome Project).

EXAMPLE 4

BRCA1 and BRCA2 Sample Construction and Preparation

This example describes methods used to generate diagnostic samples for detecting mutations in the BRCA1 and BRCA2 genes. The methods are similar to those described in Example 1 for the CFTR gene. Although particular mutations are described, one skilled in the art will recognize that similar methods can be used to introduce other BRCA1 or BRCA2 mutations. In addition, using methods similar to those described in this example, multiple mutations can be made to a single target sequence through the addition of multiple characterized plasmids each containing a single mutation. Similarly, a single plasmid can be manipulated to contain more than one mutation in a target sequence.

The 6174delT BRCA2 mutation can be used to generate a synthetic target mutant BRCA2 sequence. Fragments of BRCA2 that contained the mutation site of interest (2-4 kb) were PCR amplified from human BAC DNA (ResGen, Birmingham, Ala.) containing the wild-type (non-mutated) BRCA2 gene. BAC clone CTD 2343K5 served as the source of BRCA2 nucleic acid material for PCR amplification.

A 3 kb fragment of wild-type BRCA2 was PCR amplified, and cloned into a shuttle vector. Site-directed mutagenesis as described in Example 1 can be used to insert the 6174delT BRCA2 mutation (or any other target mutation). Plasmids containing the target sequence containing the 6174delT BRCA2 mutation can be identified by sequence analysis of the exon of interest and restriction digest pattern analysis.

Artificial positive control samples are formulated by combining equimolar ratios of the plasmid containing the mutant sequence, and the BAC containing the wild-type sequence. In addition, carrier DNA, such as salmon sperm DNA can be added for bulk, for example to bring the concentration to the target amount.

For the BRCA1 gene, a large deletion can be introduced into the BRCA1 gene through homologous recombination in tissue culture, for example using the methods described in Example 5. Fragments of BRCA1 that would result in deletion of approximately 2 kb of BRCA1 including exon 2 were PCR amplified from human BAC DNA (ResGen, Birmingham, Ala.) containing the wild-type (non-mutated) BRCA1 gene. BAC clone CTD-3199J23 served as the source of BRCA1 nucleic acid material for PCR amplification. This region can then be cloned into a cloning vector (such as pPNT), and the vector introduced into a cell to permit homologous recombination and deletion of about 2 kb of BRCA1 including exon 2. Particular exemplary methods are provided in Example 5.

Artificial positive control samples are formulated by isolating genomic DNA from the cells. In addition, carrier DNA, such as salmon sperm DNA can be added for bulk, for example to bring the concentration to the target amount (such as 50 μg/20 μl). Samples or cells can be analyzed to confirm that they contain the target mutation, for example by sequencing, assaying with a PCR/restriction digest assay or standard reverse line blot technology.

These control samples can be used as a positive control in a diagnostic assay to screen for mutations in a BRCA1 or BRCA2 gene, for example using the methods described in Example 7.

EXAMPLE 5

Mutating a Target Sequence Using Homologous Recombination

This example describes particular exemplary homologous recombination methods that can be used to introduce a mutation into a target sequence, such as a sequence associated with genetic disease. Methods are also provided for generating a null mutation of a target sequence. Although a particular example is described for introducing a mutation into CFTR, one skilled in the art will recognize that similar methods can be used to introduce a mutation into any target sequence of interest.

In particular examples, the region encompassing the sequence of interest is at least 2 kb in length, such as 2-4 kb. Because homologous recombination divides the transgene into two separate fragments (with an antibiotic resistance marker, such as $neo^R$, in the middle), the region encompassing the sequence of interest is inserted into the cloning vector in two pieces (FIG. 4). In one example, the target mutation is introduced into the outer end of one of the arms, so that its successful incorporation into the recipient genome can easily be monitored with a simple, short PCR amplification, using one primer hybridizing to the adjacent endogenous flanking region and the other primer a short way internal of the construct but encompassing the critical mutation.

For example, two targeting arms for each mutation site of interest can be generated, a long arm, 4-6 kb in size, and a short arm, 2-4 kb in size. These targeting arms, contiguous in sequence, can be PCR amplified from a wild-type sequence. For example, to generate a positive control sample for CFTR, the arms can be PCR amplified from human BAC DNA (ResGen, Birmingham, Ala.) containing the CFTR gene. BAC clones CIT-B 068P20 (AC000111) and CIT-B 133K23 (AC000061) which together contain the complete CFTR gene and flanking sequences can serve as the source of CFTR nucleic acid material for PCR amplification.

The resulting arms are cloned into a cloning vector, such as the pPNT vector (Stratagene, La Jolla, Calif.). This vector can include a multiple cloning site and a $neo^R$ gene cassette (or other antibiotic resistance sequence) and linked tk gene. If the region encompassing the gene of interest containing the mutation is available, the mutated sequence can be cloned into the vector directly. However, if the mutation is not available, for example a rare mutation, site-directed mutagenesis can be used to introduce the target mutation into a wild-type sequence. For example, after cloning the wild-type sequence into the plasmid, site directed mutagenesis can be used to introduce the mutation into the wild-type sequence (for example see Example 1). Briefly, two mismatched primers are used to amplify the wild-type sequence using PCR, one of which introduces the target mutation while the other destroys one of the restriction digest sequences in the multiple cloning site. Only the successfully mutated plasmids will be resistant to cutting with that particular restriction enzyme and can then go on to transform mismatch-repair-deficient BMH71-18 *E. coli* host cells, from which the mutated sequence can be grown in large amounts.

The resulting vector is introduced into a recipient cell, such as the HepG2, PZ-HPV-7, or HEK cell line. In one example, the cell is a lymphoblastoid cell. Any method can be used to introduce the homologous recombination vector into the cell. In a particular example, the FuGENE-6 lipid reagent (Roche Molecular Biochemicals, Indianapolis) is used. Homologous recombinants are selected by their resistance to both G418 and gancyclovir, and the proper orientation of the transgene is further confirmed by the PCR method described above or by Southern blot.

Cell colonies screened and verified by this method can be used as a positive control as follows. To generate the artificial sample, nucleic acids are isolated from the cells, such as isolation of genomic DNA. The artificial sample includes the isolated DNA. Such an artificial positive control sample can be used during molecular genetic testing, for example in methods such as reverse dot blot hybridization with allele-specific probes, Southern blotting, allele-specific restriction endonuclease digestion, capillary electrophoresis, and DNA sequencing.

If the presence of the $neo^R$ gene in the mutant construct provides erroneous results in the artificial positive control sample, a conditional replacement system in which the $neo^R$ gene is subsequently removed can be used. For example, the cre/lox system can be used to remove the $neo^R$ gene sequence. Briefly, the insert to be removed (such as the $neo^R$ gene) is cloned between two loxP sites ("floxed") which are derived from bacteriophage P1. In the presence of P1 cre recombinase, site-specific recombination between the loxP sites occurs, resulting in excision of the sequence between them. After successful homologous recombination has occurred, transient transfection with a cre-expression vector such as pBS185 (GIBCO/BRL, Rockville, Md.) will effect removal of the unwanted sequence. The cre/lox approach can be used for artificial samples that mimic homozygosity for a specific mutation, because the homologous recombination is done twice (once for each allele). If desired, a $neo^R$ fusion linked to the Aequorea jellyfish green fluorescent protein (GFP) gene can be used to monitor successful excision of the $neo^R$ gene from recombinant cells by observing loss of fluorescence from the cells.

The cre-lox system (or other recombination system) can also be used to excise the entire recombinant gene, leaving an allele that is "null" (largely or completely deleted) for the target gene. When repeated on the opposite allele, a completely null cell line can be generated (that is, one lacking any functional gene). Therefore, provided by this disclosure are null cell lines containing one or two null target genes. These null cells, as well as nucleic acids isolated from these null cells, can be used as a positive control.

EXAMPLE 6

Generation of a Positive Control Composition

This example provides a method that can be used to generate an artificial positive control that includes a synthetic mutated target sequence. One skilled in the art will appreciate that similar methods can be used to generate a positive control composition that includes a non-infectious microbial nucleic acid sequence.

A target sequence, such as a sequence known to be associated with a disease, is mutated to include one or more mutations associated with a disease. For example, if the disease is CF, the target sequence is CFTR (or a fragment thereof), and the mutation could include one or more of the following: G149R, L206W, G551D, S945L, R1070W, N1303K, D1152H, 3272-26A→G, S1235R, 3120+1G→A, ΔF508, ΔI507, 621+1G>T, G85E, 1078delT, R553X, G542X, R117H, R334W, 3849+10 kb C>T, R1162X, G551D, 1717−1G>A, R347P, 2789+5G>A, 2184delA, W1282X, A455E, 711+1G>T, 3659delC, 3120+1G>A, N1303K, R560T, 1898+1G>A, and I148T. The target sequence need not include the full-length sequence, and can include fragments thereof, such as those that are at least 100 nucleotides, such as 100-4000 nucleotides. Methods of mutating as sequence are known, such as site-directed mutagenesis, homologous recombination, and others. The target sequence can be cloned into a vector, such as a standard cloning vector (for example pCR2.1 and pCRII), and then mutated, or first mutated and then cloned into a cloning vector.

A synthetic target control sequence that includes the gene region of interest is present in a vector, such as a BAC. BACs containing many human genes (or fragments thereof), are publicly available. Alternatively, such a construct can be generated using standard cloning methods.

To generate a positive control sequence for a heterozygous mutation, the synthetic mutated target sequence and synthetic control gene region of interest are combined at a 1:1 molar ratio. Carrier DNA, such as salmon sperm DNA, can be further added to increase the DNA concentration to an amount similar to that found in a human clinical sample to be analyzed, such as at least 1 µg carrier DNA/2 µl sample, such as 50 µg DNA/20 µL.

To generate a positive control sequence for a homozygous mutation, the synthetic mutated target sequence and carrier DNA are combined. The carrier DNA is added to increase the DNA concentration to an amount similar to that found in a human clinical sample to be analyzed, such as at least 1 µg carrier DNA/2 µl sample, such as 50 µg DNA/20 µL.

EXAMPLE 7

Methods of Diagnosis

This example describes exemplary methods that can be used to determine whether a subject has a genetic mutation, for example to diagnose a disease in a subject. These methods take advantage of the artificial positive control samples described herein, which behave very similar to a control sample obtained from a subject in commonly used methods for molecular genetic testing. Although particular examples are provided for identifying BRCA2 mutations, for example to diagnose breast or ovarian cancer, the disclosure is not limited to breast/ovarian cancer and BRCA2 mutations. Similarly, although particular examples are provided for identifying CFTR mutations, for example to diagnose CF, the disclosure is not limited to CF and CFTR mutations. Based on the information provided in this example, one can determine whether a subject (or a microbe) has any known genetic mutation, using the disclosed positive control samples.

A sample from a subject is analyzed to determine whether the one or more genetic mutations are present. For example, a blood sample (or fraction thereof) can be obtained from the subject (such as at least 1 ml, at least 5 mls, 5 mls, or 1-10 mls) using standard venous puncture methods. The sample can be used directly, or the DNA in the sample isolated. In an example where a microbe sequence is analyzed, a sample can be obtained from the subject and cultured to obtain purified microbes. DNA can be isolated from the microbe for analysis, or the microbe can be used directly. The sample is subjected to a genetic screening assay, which permits detection of the target mutation. Any such method can be used, such as reverse dot blot hybridization with allele-specific probes, Southern blotting, allele-specific restriction endonuclease digestion, capillary electrophoresis, and DNA sequencing.

The method also includes using the same genetic screening assay used above to determine whether the mutation is present in the disclosed artificial positive control composition is detected by the method. If the mutation is detected in both the subject (or microbe) and the positive control sample, this indicates that the subject (or microbe) has the mutation. If the mutation is not detected in the subject (or microbe) sample, but detected in the positive control sample, this indicates that the subject (or microbe) does not have the mutation.

In one example, a single mutation is screened for. For example, if the subject is being screened for the presence of the 6174delT in BRCA2 mutation, the mutated target sequence in the artificial positive control sample also includes the 6174delT in BRCA2 mutation, and the synthetic control sequence includes a region of BRCA2 DNA that includes the 6174T position. If the 6174delT mutation is detected in both the subject and the positive control sample, this indicates that the subject has the mutation. If the 6174delT mutation is not detected in the subject, but detected in the positive control sample, this indicates that the subject does not have the mutation. However, if the 6174delT mutation is not detected in the positive control sample, no conclusive determination can be made as to the genetic status of the subject, as this indicates that the positive control is functioning as a proper control in the particular assay (or under the particular assay conditions) used.

Despite the large number of mutations spread all across the CFTR gene, CF has not been subject to testing by DNA sequencing assays because they are too laborious and expensive for what is often a screening test. Instead, individual mutations are typically detected one at a time or in a multiplex panel by hybridization with allele-specific oligonucleotide probes (for example see Wall et al. *Hum. Mutat.* 5:333-8, 1995; DeMarchi et al. *Arch. Pathol. Lab. Med.* 118:26-32, 1994; Grody et al. *Am. J. Hum. Genet.* 60:935-47, 1997), or by electrophoretic fragment analysis (Chong and Thibodeau *Mayo Clin. Proc.* 65:1072-6, 1990). The disclosed methods permit screening of multiple mutations simultaneously, for example screening of 25 different CFTR mutations associated with CF.

In one example, the following methods are used to determine if one or more of 25 different CFTR mutations are present in a subject. In one example, the 25 CFTR mutations include: ΔF508, ΔI507, 621+1G>T, G85E, 1078delT, R553X, G542X, R117H, R334W, 3849+10 kb C>T, R1162X, G551D, 1717−1G>A, R347P, 2789+5G>A, 2184delA, W1282X, A455E, 711+1G>T, 3659delC, 3120+1G>A, N1303K, R560T, 1898+1G>A, and I148T. A blood sample is obtained from the subject as described above, and a diagnostic assay (such as ASO probes on reverse hybridization strips, oligonucleotide ligation assay, restriction enzyme digestion, or DNA microarray or microbead hybridization) used to identify the 25 mutations.

In addition, the artificial positive control sample (which can be a single sample with all 25 mutations [for example each mutation on a different vector], or at least two samples with the 25 mutations divided between them [for example with at least one vector containing more than one mutation]), would be screened using a diagnostic assay to confirm that the 25 mutations can be detected with the particular assay. For example, if the subject is being screened for the presence of the ΔF508, ΔI507, 621+1G>T, G85E, 1078delT, R553X, G542X, R117H, R334W, 3849+10kb C>T, R1162X, G551D, 1717−1G>A, R347P, 2789+5G>A, 2184delA, W1282X, A455E, 711+1G>T, 3659delC, 3120+1G>A, N1303K, R560T, 1898+1G>A, and I148T CFTR mutations, the mutated target sequence in the artificial positive control sample also includes the ΔF508, ΔI507, 621+1G>T, G85E, 1078delT, R553X, G542X, R117H, R334W, 3849+10kb C>T, R1162X, G551D, 1717−1G>A, R347P, 2789+5G>A, 2184delA, W1282X, A455E, 711+1G>T, 3659delC, 3120+1G>A, N1303K, R560T, 1898+1G>A, and I148T CFTR mutations.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method of generating a positive control sample for detecting cystic fibrosis, the method comprising:
   providing a composition comprising a synthetic target sequence comprising at least one CFTR mutation and a synthetic target control sequence that includes a region of a CFTR gene which does not include the at least one CFTR mutation, wherein the at least one CFTR mutation comprises a ΔF508, ΔI507, 621+1G>T, G85E, 1078delT, R553X, G542X, R117H, R334W, 3849+10kb C>T, R1162X, G551D, 1717–1G>A, R347P, 2789+5G>A, 2184delA, W1282X, A455E, 711+1G>T, 3659delC, 3120+1G>A, N1303K, R560T, 1898+1G>A, or I148T CFTR mutation; and
   carrier DNA, wherein the carrier DNA is at a concentration of at least 50 μg/20 μl in the composition, thereby generating a positive control sample for detecting cystic fibrosis.

2. The method of claim 1, wherein the synthetic target sequence and the synthetic target control sequence are present on separate polynucleotide molecules.

3. The method of claim 2, wherein the separate polynucleotide molecules comprise vectors.

4. The method of claim 1, wherein the method further includes introducing said at least one CFTR mutation into a target sequence, thereby generating the synthetic target sequence.

5. The method of claim 4, wherein said introducing comprises site-directed mutagenesis of the target sequence.

6. The method of claim 4, wherein said introducing comprises:
   mutagenizing a target wild-type sequence that includes a region of a CFTR gene, wherein the target wild-type sequence is present in a vector.

7. The method of claim 6, wherein the method further includes introducing the target wild-type sequence that includes the region of the CFFR gene into the vector.

8. The method of claim 6, furthering comprising detecting at least one CFTR genetic mutation in a sample obtained from a subject, wherein said detecting comprises analyzing the sample obtained from the subject and the generated positive control sample.

9. The method of claim 1, wherein the synthetic target sequence comprises twenty five (25) CFTR mutations comprising a ΔF508, ΔI507, 621+1G>T, G85E, 1078delT, R553X, G542X, R117H, R334W, 3849+10kb C>T, R1162X, G551D, 1717–1G>A, R347P, 2789+5G>A, 2184delA, W1282X, A455E, 711+1G>T, 3659delC, 3120+1G>A, N1303K, R560T, 1898+1G>A, and I148T CFTR mutations.

10. The method of claim 8, wherein the synthetic target sequence comprises twenty five (25) CFTR mutations comprising a ΔF508, ΔI507, 621+1G>T, G85E, 1078delT, R553X, G542X, R117H, R334W, 3849+10kb C>T, R1162X, G551D, 1717–1G>A, R347P, 2789+5G>A, 2184delA, W1282X, A455E, 711+1G>T, 3659delC, 3120+1G>A, N1303K, R560T, 1898+1G>A, and I148T CFTR mutations, thereby allowing detection of 25 different CFTR mutations simultaneously.

* * * * *